(12) United States Patent
Abokela et al.

(10) Patent No.: US 11,575,999 B2
(45) Date of Patent: Feb. 7, 2023

(54) SYSTEMS AND METHODS FOR HEARING ASSESSMENT AND AUDIO ADJUSTMENT

(71) Applicant: Meta Platforms Technologies, LLC, Menlo Park, CA (US)

(72) Inventors: Haytham Mohamed Fayek Abdallah Abdelrehim Abokela, Kirkland, WA (US); Antonio John Miller, Woodinville, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/745,287

(22) Filed: Jan. 16, 2020

(65) Prior Publication Data
US 2021/0227338 A1    Jul. 22, 2021

(51) Int. Cl.
*H04R 25/00* (2006.01)
*A61B 5/12* (2006.01)
*A61B 5/00* (2006.01)

(52) U.S. Cl.
CPC .......... *H04R 25/507* (2013.01); *A61B 5/121* (2013.01); *H04R 2225/43* (2013.01)

(58) Field of Classification Search
CPC ............ H04R 2225/00; H04R 2225/43; H04R 2225/49; H04R 2225/53; H04R 2225/41; H04R 2225/39; H04R 2225/33; H04R 2225/31; H04R 2225/025; H04R 2225/023; H04R 2225/0216; H04R 25/00; H04R 25/50; H04R 25/505; H04R 25/507; H04R 25/554; H04R 25/407; H04R 25/558; H04R 25/552; H04R 25/30; A61B 5/121; A61B 5/12; A61B 5/123; A61B 5/125; A61B 5/126; A61B 5/6898
USPC ......... 704/270, 271; 381/312–331, 23.1, 60; 700/94
See application file for complete search history.

(56) References Cited

U.S. PATENT DOCUMENTS

| 7,467,081 B2 * | 12/2008 | Alshawi .................. G06F 40/45 704/10 |
| 2007/0118352 A1 * | 5/2007 | Alshawi .............. H04M 3/4936 704/2 |
| 2018/0213339 A1 * | 7/2018 | Shah ..................... H04R 25/558 |
| 2019/0379985 A1 * | 12/2019 | Thomsen ............. H04R 25/505 |

\* cited by examiner

*Primary Examiner* — Leshui Zhang
(74) *Attorney, Agent, or Firm* — Foley & Lardner LLP

(57) ABSTRACT

An audio system for user hearing assessment includes one or more audio capture devices, and processing circuitry. The one or more audio capture devices are configured to capture audio of a conversation of a user and convert the audio to audio signals. The processing circuitry is configured to use the audio signals to identify multiple conditions associated with user hearing difficulty. The conditions include any of words, phrases, frequencies, or phonemes, and environmental audio conditions that are followed by an indication of user hearing difficulty. The processing circuitry is configured to generate a hearing profile for the user based on the identified conditions associated with user hearing difficulty. The processing circuitry is configured to adjust an operation of an audio output device using the hearing profile to reduce a frequency of user hearing difficulty if the user requires audio enhancement.

12 Claims, 8 Drawing Sheets

SYSTEMS AND METHODS FOR HEARING ASSESSMENT AND AUDIO ADJUSTMENT

FIELD OF DISCLOSURE

The present disclosure is generally related to audio systems, including but not limited to head wearable audio systems.

BACKGROUND

Hearing assessment is typically required to obtain a characterization of an individual's hearing ability. An understanding of an individual's hearing ability may be crucial for enhancing the individual's ability. Audio systems typically do not take into account the individual's hearing ability, but rather produce sound for the user without accounting for hearing difficulties that the user may experience across various frequencies. Hearing assessment for an individual is typically performed in a controlled lab setting.

SUMMARY

Various embodiments disclosed herein are related to an audio system for user hearing assessment. In some embodiments, the audio system includes one or more audio capture devices, and processing circuitry. In some embodiments, the one or more audio capture devices are configured to capture audio of a speech of a user and convert the audio to audio signals. In some embodiments, the processing circuitry is configured to use the audio signals to identify multiple conditions associated with user hearing difficulty. In some embodiments, the conditions include any of words, phrases, frequencies, or phonemes, and environmental audio conditions that are followed by an indication of user hearing difficulty. In some embodiments, the processing circuitry is configured to generate a hearing profile for the user based on the identified conditions associated with user hearing difficulty. In some embodiments, the processing circuitry is configured to adjust an operation of an audio output device using the hearing profile to reduce a frequency of user hearing difficulty if the user requires audio enhancement.

Various embodiments disclosed herein are related to an audio system for user hearing assessment, according to some embodiments. In some embodiments, the audio system includes one or more audio capture devices configured to capture audio of an individual user's speech and convert the audio to audio signals. In some embodiments, the audio system includes processing circuitry. The processing circuitry can be configured to use the audio signals and a neural network to generate a customized hearing profile for the individual user. In some embodiments, the hearing profile indicates an ability of the user to hear different audio frequencies or phonemes. In some embodiments, the processing circuitry is configured to obtain multiple hearing profiles of other users of a population of users. In some embodiments, the processing circuitry is configured to obtain a ranking of the customized hearing profile and the multiple hearing profiles of the other users to identify one or more users of the population that suffer from hearing difficulty. In some embodiments, the processing circuitry is configured to provide an indication to the individual user if the individual user is one of the users of the population that suffers from hearing difficulty.

Various embodiments disclosed herein are related to a method for assessing a user's hearing ability and improving audio output of a sound producing device. In some embodiments, the method includes obtaining information of a user's speech using audio signals. In some embodiments, the method also includes identifying one or more indications of hearing difficulty using the information and multiple conditions preceding the indication of hearing difficulty. In some embodiments, the method includes generating a customized hearing profile for the user based on the one or more indications of hearing difficulty and the multiple conditions. In some embodiments, the method includes adjusting audio output of a sound producing device using the customized hearing profile to reduce a frequency of user hearing difficulty events.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing.

DETAILED DESCRIPTION

Overview

Figure 1:
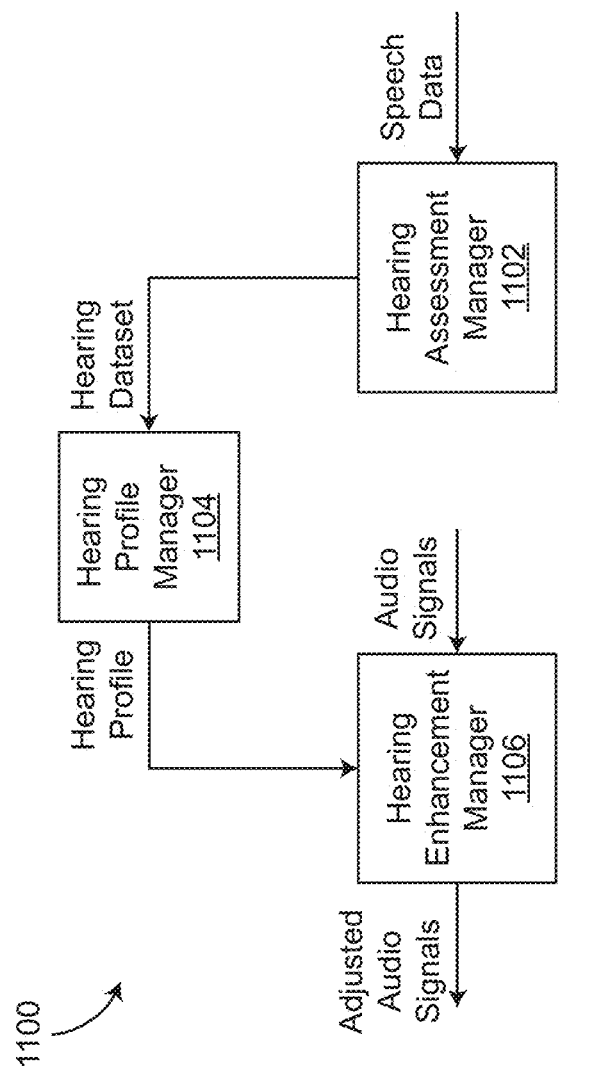
FIG. 1 is a block diagram of a system for user hearing assessment and adjustment, according to some embodiments.

Before turning to the FIGURES, which illustrate certain embodiments in detail, it should be understood that the present disclosure is not limited to the details or methodology set forth in the description or illustrated in the FIGURES. It should also be understood that the terminology used herein is for the purpose of description only and should not be regarded as limiting.

Referring generally to the FIGURES, systems and methods for passive hearing assessment and improvement are shown, according to various embodiments. A system can include multiple sub-systems that cooperatively define a population. In some embodiments, the sub-systems cooperatively exchange data between each other. For example, each sub-systems may be associated with a particular user, and the sub-systems may exchange data only if the particular user opts-in for data sharing.

Each sub-system includes a controller, one or more audio capture device(s), one or more audio output device(s), and a user interface, according to some embodiments. In some embodiments, the controller is or includes processing circuitry, a processing unit, etc. The controller may include a hearing assessment manager or a system for passive hearing assessment, a hearing profile manager, or a system for hearing profile characterization, and a hearing enhancement manager, or a system for passive continuous hearing enhancement.

In some embodiments, the controller is configured to receive, obtain, etc., audio signal(s) from the one or more audio capture device(s). For example, the audio capture device(s) and/or the audio input device(s) can be configured as part of a head wearable device (e.g., an augmented reality headset, a virtual reality headset, a mixed reality headset, wearable headphones, etc.), or may be part of an infrastructure of the head wearable device.

In some embodiments, the hearing assessment manager of the controller is configured to obtain audio signals from the audio capture device(s) over at least a training time period. The hearing assessment manager may perform speech recognition on audio data obtained from the audio capture device(s). In some embodiments, the hearing assessment manager is configured to transcribe the audio data to generate text data. The hearing assessment manager can be configured to mine, search, or identify spoken words, phrases, phonemes, etc., that indicate hearing difficulty and/or hearing ability in the text data. For example, the hearing assessment manager may user a predetermined list of words, phrases, sentences, etc., that indicate hearing difficulty or that indicate hearing ability. In some embodiments, the hearing assessment manager is configured to use a neural network, a machine learning method, etc., or artificial intelligence to identify hearing difficulty and/or hearing ability based on the text data. In some embodiments, the controller passively and continuously performs its functionality after the training time period to continuously evaluate the user's hearing ability and adjust audio output to reduce hearing difficulty occurrences.

In some embodiments, the hearing assessment manager is configured to record environmental conditions, and text data preceding the hearing difficulty indication and/or preceding the hearing ability indication. Hearing assessment manager can store the environmental conditions and text data preceding the hearing difficulty or hearing ability indication in a database. In some embodiments, hearing assessment manager monitors the user's conversation or speech over a time period and generates a set of data (e.g., training data or hearing data) that is stored in the database. The data may be used as training data to initially create a model, or may be used after the model is created/generated to self-evaluate a current state of the sub-system.

In some embodiments, the hearing profile manager is configured to use the hearing data stored in the database to generate, define, construct, estimate, calculate, etc., a hearing difficulty prediction model and/or a user audiogram. For example, the hearing profile manager may use artificial intelligence, a neural network, and/or machine learning to generate or define a prediction model that can predict whether a user will have difficulty hearing given an input of environmental conditions and/or text data. In this way, the prediction model can be tailored for the specific user and predicts hearing difficulty for the associated user. In some embodiments, the hearing profile manager is configured to use the hearing data and/or the prediction model to determine, calculate, generate, estimate, etc., a hearing profile or an audiogram for the particular user. In some embodiments, the audiogram indicates a user's hearing ability across various frequencies.

The hearing profile manager may provide the audiogram to the hearing enhancement manager for use in determining audio adjustments, and/or to the hearing assessment manager for ranking. In some embodiments, the hearing assessment manager is configured to receive the audiogram from the hearing profile manager and one or more other audiograms from a cloud computing system. For example, the other audiograms may be population audiograms corresponding to different users in the population. In some embodiments, the hearing assessment manager is configured to user the population audiograms and the user audiogram that is generated based on the hearing data to rank the user's hearing ability relative to other users in the population.

In some embodiments, the hearing enhancement manager is configured to use the user's audiogram and/or population audiograms to determine audio adjustments for the audio output device(s). In some embodiments, the hearing enhancement manager is configured to function in a closed-loop manner so that the hearing enhancement manager uses feedback from the audio capture device(s) to continually adjust, update, improve, etc., the audio adjustments of the audio output device(s) until no further audio adjustment(s) are required.

Advantageously, the systems and methods described herein may be configured to passively assess the user's hearing abilities (e.g., based on audio data), provide a notification to the user regarding the user's hearing abilities (e.g., if it is determined that the user suffers from hearing loss across one or more frequencies), and actively adjust audio output that is provided to the user to reduce a likelihood or frequency of hearing difficulty events. In some embodiments, the systems and methods described herein are configured to generate and use a user audiogram to identify adjustments for one or more sound producing devices so that it is easier for the user to hear sound output. For example, if the user audiogram indicates that the user has difficulty hearing high frequency noises, the systems and methods described herein may amplify or adjust the frequency of particular sounds or noises before outputting the sounds to the user, thereby reducing the likelihood that the user will have difficulty hearing the sounds.

It should be understood that while the systems and methods described herein (e.g., the hearing assessment manager, the hearing profile manager, and/or the hearing enhancement manager) are shown and described as being implemented on a single processing unit, the functionality or processing may be performed or distributed across multiple processing units. For example, the functionality of the hearing profile manager, the hearing assessment manager, and the hearing enhancement manager may be performed on separate processing units that cooperatively function by exchanging information therebetween and operating the audio capture device(s) and/or the audio output device(s).

Systems, Methods, and Devices for Passive Hearing Assessment and Audio Improvement
System Overview Referring particularly to FIGS. 1-9, systems and methods for passive hearing assessment and audio improvement are shown, according to some embodiments. In some embodiments, the systems and methods described herein are configured to obtain, monitor, detect, sense, etc., audio data of a user's conversation or speech (only if the user opts-in to the functionality of the systems and methods described herein) and generate, calculate, determine estimate, etc., an audiogram for the user. The systems and methods may be implemented on a wearable device (e.g., headphones, a head wearable display device, etc.) and may be configured to use the user's audiogram to adjust sound output by a speaker or sound producing device to reduce a frequency of user hearing difficulty events.

Referring particularly to FIG. 1, a system 1100 for performing hearing assessment and hearing enhancement (e.g., audio enhancement) is shown, according to some embodiments. System 1100 includes a hearing assessment manager 1102, a hearing profile manager 1104, and a hearing enhancement manager 1106. In some embodiments, hearing assessment manager 1102 is the same as or similar to hearing assessment manager 500 as described in greater detail below with reference to FIGS. 3-6. In some embodiments, hearing profile manager 1104 is the same as or similar to hearing profile manager 600 as described in greater detail below with reference to FIGS. 3-6. In some embodiments, hearing enhancement manager 1106 is the same as or similar to hearing enhancement manager 700 as described in greater detail below with reference to FIGS. 3-6. System 1100 may be implemented on a processing circuit, a processing unit, a computer system, a controller, a microprocessor, a digital processing unit, distributed across multiple processing circuits, etc., or any other processing systems described in the present disclosure. In some embodiments, system 1100 is implemented as a head wearable system (e.g., a head wearable audio system). In some embodiments, system 1100 is a sub-system or a system of an augmented reality system, a virtual reality system, a mixed reality system, etc.

System 1100 is configured to passively listen to a user's conversation or speech (e.g., if the user opts-in for the functionality of system 1100), monitors the user's conversation or speech for signs or indications of hearing difficulty (e.g., by mining one-on-one conversations for phrases that indicate difficulty hearing in benign non-noisy environments), predicts a personalized hearing profile (e.g., an audiogram), and determines hearing enhancements. In some embodiments, system 1100 operates in a closed-loop manner by validating and self-correcting the proposed hearing enhancements. For example, system 1100 may re-perform the functionality of monitoring the user's conversation, predicting the personalized hearing profile, and proposing additional hearing enhancements.

Hearing assessment manager 1102 is configured to receive speech data from a microphone, a sound capture device, another system, another sub-system, etc. In some embodiments, the speech data is of a user's one-on-one conversation with another individual. For example, the speech data may be audio of speech of the user for which system 1100 is configured. In some embodiments, hearing assessment manager 1102 is configured to obtain speech data under predefined environmental conditions that do not pose hearing challenges to a person with nominal hearing (e.g., low noise levels). Hearing assessment manager 1102 may perform speech-to-text analysis to convert the speech data to textual data of the user's conversation. In some embodiments, hearing assessment manager 1102 recognizes, detects, senses, etc., spoken words or phrases in the textual or speech data that indicates hearing difficulty. Hearing assessment manager 1102 may also identify, recognize, detect, sense, etc., spoken words or phrases that are not followed by indications of hearing difficulty. In some embodiments, hearing assessment manager 1102 is configured to collect, store, and mark the spoken words or phrases along with environmental conditions at the time as either being followed by an indication of hearing difficulty, or as not being followed by an indication of hearing difficulty.

Hearing assessment manager 1102 can generate, produce, construct, etc., a database of environment conditions and spoken words or phrases along with markings or labels of hearing difficulty (or lack thereof) and may aggregate this data over a time interval. In some embodiments, hearing assessment manager 1102 receives data from other systems 1100 so that hearing assessment manager 1102 or system 1100 may learn across multiple systems.

Hearing assessment manager 1102 provides the database of environmental conditions and spoken words or phrases along with markings or labels of hearing difficulty (or hearing ability), shown as hearing dataset, to hearing profile manager 1104. In some embodiments, hearing profile manager 1104 is configured to receive the hearing dataset and use the hearing dataset to characterize, quantify, etc., the user's hearing ability. For example, hearing profile manager 1104 can be configured to generate, construct, define, estimate, etc., a hearing profile or an audiogram for the user based on the hearing dataset received from hearing assessment manager 1102. In some embodiments, hearing profile manager 1104 uses a neural network, machine learning, a model, performs a process, etc., to generate the hearing profile for the user based on the hearing dataset received from hearing assessment manager 1102. In some embodiments, hearing profile manager 1104 outputs the hearing profile or the audiogram to hearing enhancement manager 1106. The hearing profile may identify or characterize the user's hearing ability across various frequencies. In some embodiments, hearing profile manager 1104 and/or hearing assessment manager 1102 are configured to generate a model that can predict whether a user will be able to hear a particular word, phrase, phoneme, group of phonemes, etc. In some embodiments, hearing profile manager 1104 is configured to use the model to generate the hearing profile.

Hearing enhancement manager 1106 is configured to receive the hearing profile or the audiogram from hearing profile manager 1104 and use the hearing profile to generate audio adjustments to facilitate reducing occurrences of hearing difficulty for the user. In some embodiments, hearing enhancement manager 1106 is configured to receive audio signals and output adjusted audio signals using the audio adjustments or using the hearing profile. In some embodiments, hearing enhancement manager 1106 is configured to also identify one or more frequencies that the user has difficulty hearing. In some embodiments, hearing enhancement manager 1106 is configured to report across which frequencies that the user has hearing difficulty. Hearing enhancement manager 1106 can also be configured to operate a visual and/or aural display device to provide the user with a notification or report of the user's hearing ability. In some embodiments, hearing enhancement manager 1106 uses the audio signals and adjusts, or amplifies sound output (the adjusted audio signals) across particular frequencies that the user has difficulty hearing to reduce the likelihood that the user will experience hearing difficulty or have trouble hearing.

System 1100 can be implemented to adjust audio output of a head wearable audio device, or can provide a notification regarding the user's hearing ability. In some embodiments, system 1100 is configured to passively assess the user's hearing ability in real-time and identify frequencies, phrases, words, etc., that the user has difficulty hearing. In some embodiments, system 1100 actively adjusts, adapts, etc., the hearing profile based on additionally received speech data. System 1100 can be configured to actively adjust audio output to reduce a likelihood of hearing difficulty for the user. In some embodiments, system 1100 is configured to provide the user with a notification regarding the user's hearing ability. The notification may include what frequencies the user has difficulty hearing across, in addition to a magnitude of hearing loss that the user experiences across various frequencies. In some embodiments, the notification may prompt the user to see a hearing specialist. In some embodiments, any of the data collection (e.g., obtaining the speech data) is only performed if the user opts-in for hearing assessment and/or hearing enhancement.

Figure 2:
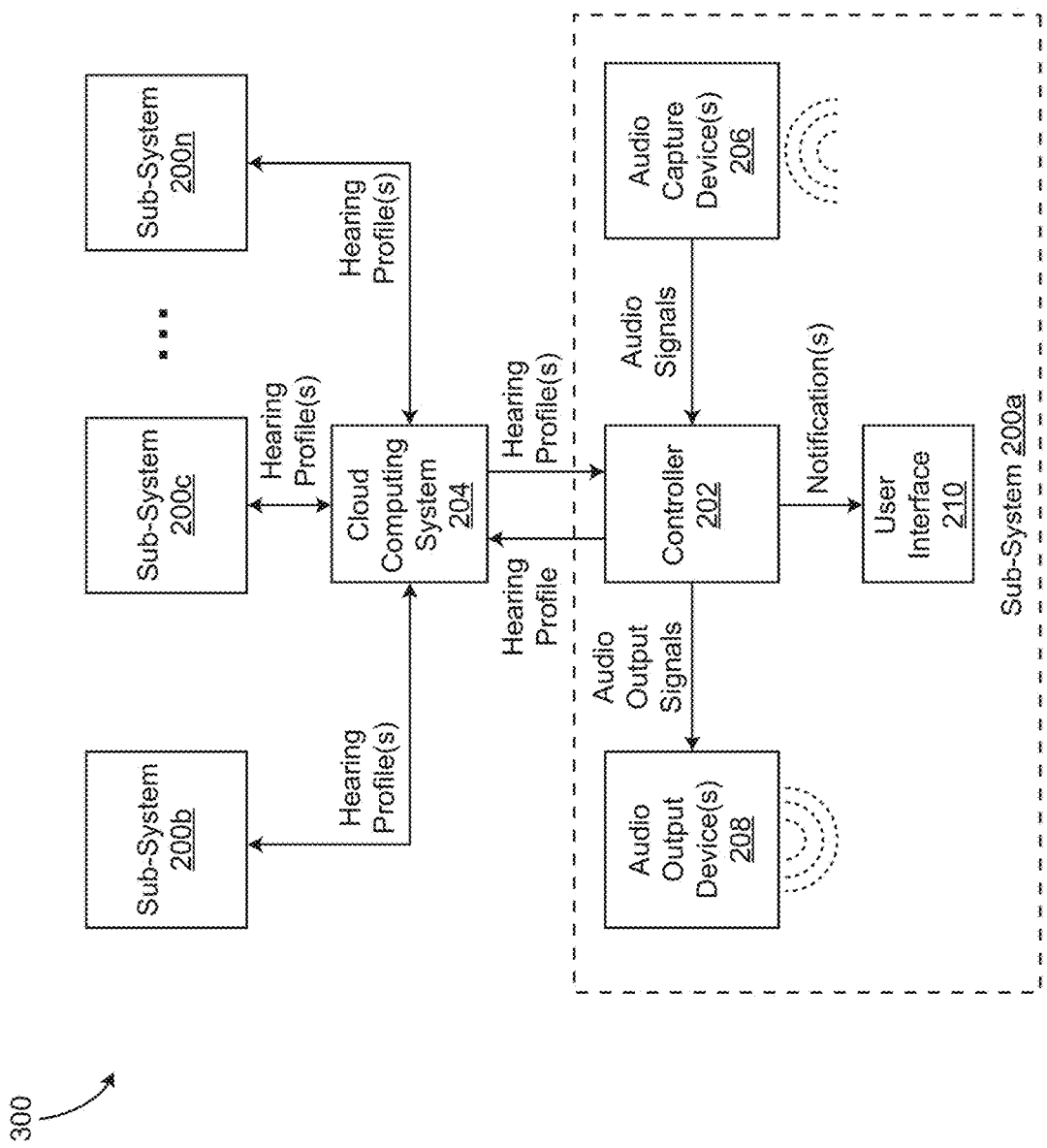
FIG. 2 is a block diagram of a system for user hearing assessment and adjustment for a population of users, according to some embodiments.

Referring particularly to FIG. 2, a system 300 is shown, according to some embodiments. System 300 includes a cloud computing system, a remote device, etc., shown as cloud computing system 204, according to some embodiments. System 300 also includes multiple sub-systems 200*a*-200*n* that are configured to communicate with cloud computing system 204. In some embodiments, each of the sub-systems 200 are configured to provide cloud computing system 204 with hearing profiles (e.g., an audiogram) for a particular user associated with the sub-system 200. For example, sub-system 200*a* may provide cloud computing system 204 with a hearing profile for a particular user (e.g., an owner, an associated user, a user of sub-system 200*a*, etc.), while sub-system 200*b* provides cloud computing system 204 with a hearing profile for a different particular user, etc. In some embodiments, cloud computing system 204 is configured to facilitate the exchange of data between the various sub-systems 200 or other remote systems, databases, cloud computing systems, devices, etc. In this way, cloud computing system 204 may facilitate the exchange of data (e.g., hearing profiles, audiograms, etc.) between the various sub-systems 200. In some embodiments, data used to generate the hearing profiles or audiograms is also exchanged between the sub-systems 200 via cloud computing system 204. In some embodiments, sub-system 200 communicate directly with each other to facilitate the exchange of data.

In some embodiments, the exchange of data (e.g., hearing profiles, audiograms, etc.) between the sub-systems 200 of system 300 only occurs if the user associated with the particular sub-system 200 opts-in to data exchange. For example, each sub-system 200 may also retrieve or receive data from the cloud computing system 204 or the other sub-systems 200 to improve, update, adjust, etc., their hearing profiles or audiograms. In some embodiments, each sub-system 200 also uses the hearing profiles or audiograms to quantitatively determine if the particular user of the sub-system 200 suffers from hearing loss and would benefit from audio adjustments to reduce hearing difficulty.

Referring still to FIG. 2, each sub-system 200 may be the same as or similar to sub-system 200*a*. Sub-system 200*a* include a controller 202, one or more audio capture device(s) 206 (e.g., microphones, transducers, etc.), and one or more audio output device(s) 208 (e.g., speakers, transducers, etc.), according to some embodiments. In some embodiments, the audio capture device(s) 206 are acoustic transducers that are configured to convert acoustic or sound waves into audio signals and provide the audio signals to controller 202. In some embodiments, the audio capture device(s) 206 and the audio output device(s) 208 are components of an infrastructure of a device that controller 202 is positioned at, associated with, performs functionality for, etc., or a device to which controller 202 otherwise corresponds. In some embodiments, audio output device(s) 208 are acoustic transducers that are configured to receive audio signals (e.g., audio output signals, adjusted audio output signals, etc.) from controller 202, or from another processing unit, and output acoustic or sound waves. Likewise, audio capture device(s) 206 can be acoustic transducers that are configured to receive acoustic or sound waves and generate audio signals for controller 202 based on the acoustic or sound waves.

Controller 202 may be configured to use the audio signals to generate an audiogram, or a hearing profile for the particular user. Controller 202 may identify if the user suffers from hearing loss using the audiogram or the hearing profile and can adjust audio output of audio output device(s) 208 to facilitate improving the user's hearing. For example, controller 202 may adjust an amplitude of a particular frequency, a particular spoken phoneme, certain sounds, certain vowels, etc., to reduce a likelihood that the user is unable to hear or understand a particular sound. In some embodiments, controller 202 is also configured to operate a user interface 210 (e.g., a display screen, a display device, a combiner, a speaker, an audio output device, etc.) to provide a notification to the user that the user suffers from some degree of hearing loss. In this way, the user may be prompted by the controller 202 to visit a hearing specialist if it is determined by controller 202 that the user suffers from hearing loss.

Controller

Figure 3:
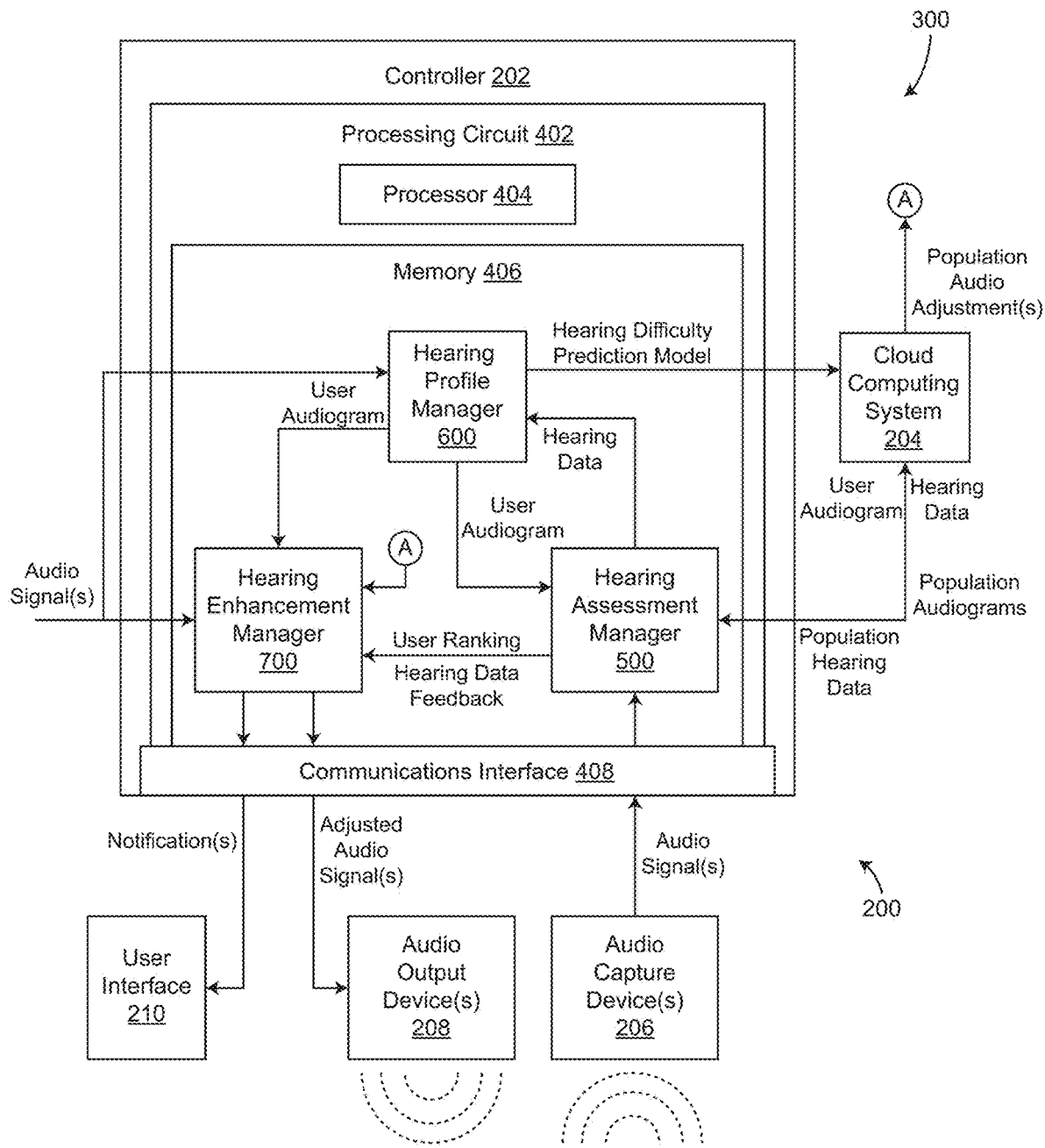
FIG. 3 is a block diagram of the system of FIG. 2 showing one of multiple sub-systems in greater detail, including a controller, according to some embodiments.

Referring particularly to FIG. 3, a portion of system 300 is shown in greater detail, according to some embodiments. Specifically, FIG. 3 shows a particular sub-system 200 and the functionality of controller 202 in greater detail, according to some embodiments. Controller 202 can include a communications interface 408 that facilitates communications (e.g., the transfer of data) into and out of the controller 202. For example, communications interface 408 may facilitate communication (e.g., wireless communication) between audio capture device(s) 206, audio output device(s) 208, cloud computing system 204, and controller 202. The communications interface 408 can be or include wired or wireless communications interfaces (e.g., jacks, antennas, transmitters, receivers, transceivers, wire terminals, etc.) for conducting data communications between the controller 202 and external systems, sensors, devices, etc. In various embodiments, communications via the communications interface 408 can be direct (e.g., local wired or wireless communications) or via a communications network (e.g., a WAN, the Internet, a cellular network, etc.). For example, the interface 408 can include an Ethernet card and port for sending and receiving data via an Ethernet-based communications link or network. In another example, the interface 408 can include a Wi-Fi transceiver for communicating via a wireless communications network. In another example, the interface 408 can include cellular or mobile phone communications transceivers. In some embodiments, the interface 408 is an Ethernet interface or a USB interface.

Still referring to FIG. 3, the controller 400 is shown to include a processing circuit 402 including a processor 404 and memory 406. The processing circuit 402 can be communicably connected to the communications interface 408 such that the processing circuit 402 and the various components thereof can send and receive data via the communications interface. The processor 404 can be implemented as a general purpose processor, an application specific integrated circuit (ASIC), one or more field programmable gate arrays (FPGAs), a group of processing components, or other suitable electronic processing components.

The memory 406 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. The memory 406 can be or include volatile memory or non-volatile memory. The memory 406 can include database components, object code components, script components, or any other type of information structure for supporting the various activities and information structures described in the present application. According to some embodiments, the memory 406 is communicably connected to the processor 404 via the processing circuit 402 and includes computer code for executing (e.g., by the processing circuit 402 and/or the processor 404) one or more processes described herein.

Referring still to FIG. 3, memory 406 includes a hearing profile manager 600, a hearing assessment manager 500, and a hearing enhancement manager 700, according to some embodiments. In some embodiments, hearing assessment manager 500 is configured to obtain, receive, detect, etc., audio signals from audio capture device(s) 206. Hearing assessment manager 500 may be configured to also receive hearing profiles, hearing data, audiograms, etc., of a population of users from cloud computing system 204. In some embodiments, hearing assessment manager 500 is configured to use the population hearing data and/or the population audiograms or the population hearing profiles to rank the user's hearing relative to other users in the population. In this way, hearing assessment manager 500 can determine if the user has poor hearing, hearing loss, etc., relative to other users in the population.

In some embodiments, the hearing profile is an audiogram. The audiogram may be generated using the hearing data obtained by hearing assessment manager 500 based on the audio signals(s) (as described in greater detail below with reference to FIG. 4). In some embodiments, the hearing profile is any dataset that quantitatively defines how well the user can hear different sound frequencies, different phonemes, different words, etc. In some embodiments, hearing assessment manager 500 is configured to obtain a database of hearing data and provide the hearing data to hearing profile manager 600. The hearing data can include indications of detected hearing difficulty (e.g., events of hearing difficulty) as well as environmental conditions, spoken words or phrases, phonemes, etc., that precede the hearing difficulty event. In some embodiments, hearing assessment manager 500 is configured to use the audio signal(s) received from audio capture device(s) 206 to detect hearing difficulty events and generate, aggregate, etc., the hearing data.

Hearing assessment manager 500 is also configured to receive the user audiogram from hearing profile manager 600 (or the hearing profile), according to some embodiments. In some embodiments, hearing assessment manager 500 is also configured to receive user audiograms relating to other users in the population from cloud computing system 204. Hearing assessment manager 500 may use the population audiograms and the user audiogram to rank the user's audiogram relative to other users in the population. In some embodiments, hearing assessment manager 500 is configured to provide a user ranking to hearing enhancement manager 700 for use in notifying the user or for use in adjusting audio output of audio output device(s) 208 to facilitate reducing a likelihood or a frequency of hearing difficulty events of the user.

Hearing profile manager 600 is configured to receive hearing data from hearing assessment manager 500 and generate the user audiogram based on the hearing data. In some embodiments, hearing profile manager 600 is configured to provide the user audiogram to hearing enhancement manager 700. Hearing enhancement manager 700 uses the user audiogram to determine audio adjustments for audio output device(s) 208.

Hearing Assessment Manager

Figure 4:
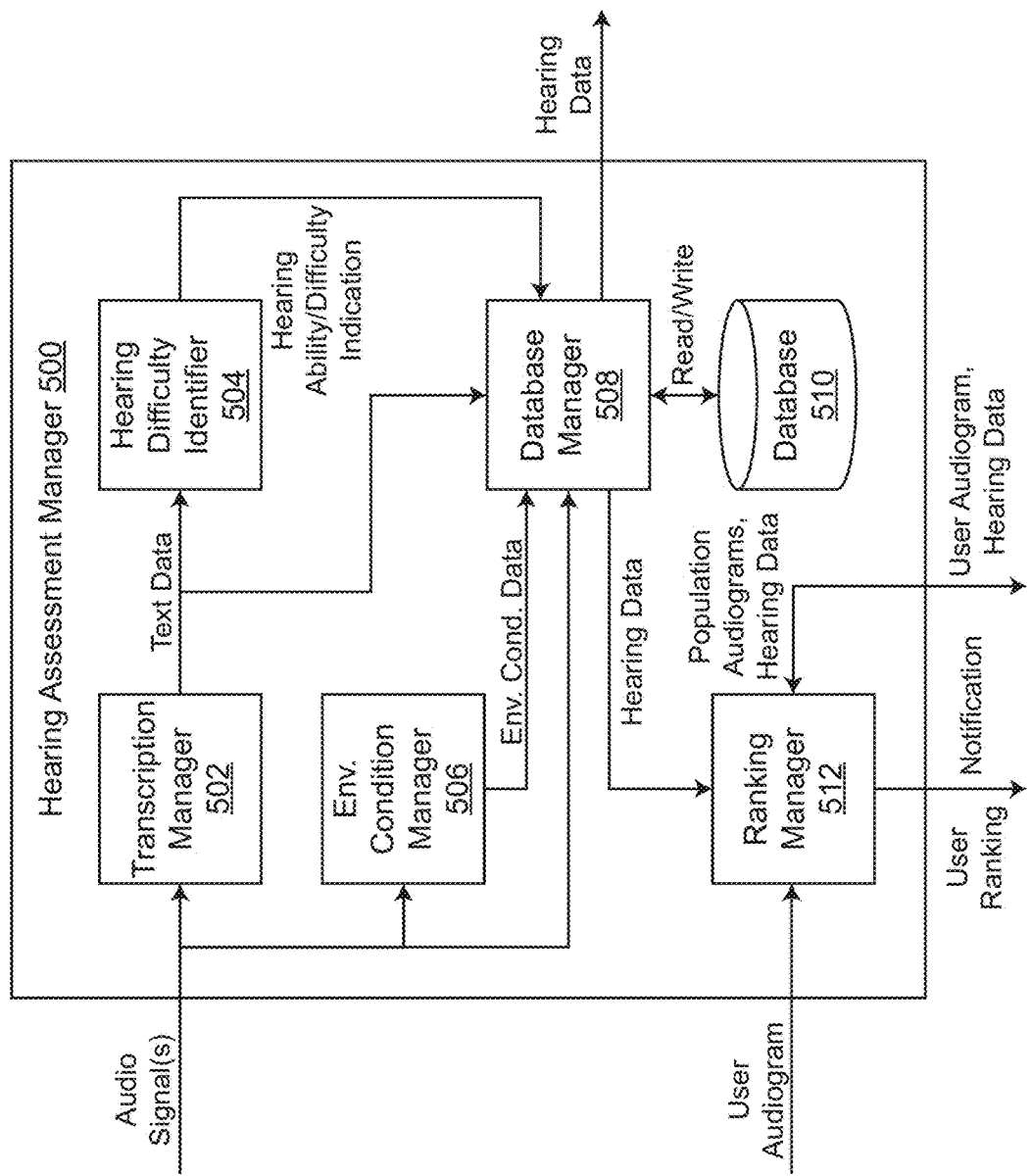
FIG. 4 is a block diagram of a hearing assessment manager of the controller of FIG. 3, according to some embodiments.

Referring particularly to FIG. 4, hearing assessment manager 500 is shown in greater detail, according to some embodiments. Hearing assessment manager 500 includes a transcription manager 502, an environmental condition manager 506, a hearing difficulty identifier 504, a database manager 508, a database 510, and a ranking manager 512, according to some embodiments.

In some embodiments, transcription manager 502 is configured to receive the audio signals(s) from audio capture device(s) 206 and convert the audio signal(s) to text. For example, the audio signal(s) or audio data may be conversational or spoken data obtained via audio capture device(s) 206. In some embodiments, conversational data is only obtained via audio capture device(s) 206 if the user opts-in to allow controller 202 to monitor conversations.

Transcription manager 502 may perform speech recognition on the audio signal(s) or the audio data to detect speakers (e.g., the user and other speakers) and generate textual information or text data. In some embodiments, transcription manager 502 uses speech recognition techniques to identify a number of speakers, different speakers, etc. Transcription manager 502 can convert the audio data into text data and provide the text data to hearing difficulty identifier 504. In some embodiments, transcription manager 502 is configured to identify when the user is speaking or when another speaker other than the user is speaking. The text data can include an indication of which speaker is speaking, and the corresponding text data, words, phrases, questions, statements, phonemes, etc. In some embodiments, transcription manager 502 is configured to perform an automatic speech recognition technique (ASR), or a speech-to-text (STT) technique to generate the text data based on the audio signals(s)/data.

Transcription manager 502 can use voice recognition techniques and/or a neural network or a machine learning technique to convert the audio data to textual data. In some embodiments, transcription manager 502 uses a pre-trained neural network or model to identify spoken words, phrases, phonemes, speakers, etc., of the audio data and to generate the text data or the transcription of the conversation. In some embodiments, transcription manager 502 uses a neural network or a machine learning model that is trained based on audio data or audio signals obtained through audio capture device(s) 206 (e.g., conversational data of the user). For example, transcription manager 502 can use Hidden Markov models, dynamic time warping (DTW) speech recognition techniques, a convolution neural network (CNN), etc., to identify spoken words, phrases, phonemes, etc., in the audio signal(s) and generate the text data.

Transcription manager 502 can be configured to receive the audio signal(s) from audio capture device(s) 206 in real-time. In some embodiments, transcription manager 502 is configured to perform its respective speech recognition functionality in real-time and generates the text data in real-time. The text data or transcription may be provided to hearing difficulty identifier 504 in real-time.

Referring still to FIG. 4, hearing difficulty identifier 504 is configured to receive the text data from transcription manager 502 and identify if a hearing difficulty event has occurred. In some embodiments, hearing difficulty identifier 504 is configured to receive the text data, and mine the text data for one or more predetermined words, phrases, questions, etc., that indicate that the user is having difficulty hearing. For example, hearing difficulty identifier 504 can include a database or a set of particular words, phrases, questions, etc., that indicate that the user is having difficulty hearing. For example, hearing difficulty identifier 504 may mine the text data for any of the phrases "Could you repeat that?", "What did you say?", "I can't hear you" etc. In some embodiments, hearing difficulty identifier 504 includes a database of the phrases that indicate hearing difficulty and monitors the text data in real-time to determine if the user has spoken any of the phrases that indicate hearing difficulty. In some embodiments, hearing difficulty identifier 504 is configured to use a neural network, a machine learning method, or a model to predict if the user has experienced hearing difficulty using the text data. In some embodiments, hearing difficulty identifier 504 also received environmental condition data from environmental condition manager 506 indicating a level of background noise. Hearing difficulty identifier 504 may identify the hearing difficulty indications using the text data and the environmental condition data. For example, if there is a large amount of background noise, hearing difficulty identifier 504 may use a different model (e.g., a model that is more sensitive or more likely to detect hearing difficulty), may mine the text data for different spoken words or phrases, etc. In this way, the functionality of hearing difficulty identifier 504 may be adjusted or change based on environmental condition data (e.g., background noise, number of speakers, etc.).

The functionality of hearing difficulty identifier 504 may also change or be automatically adjusted based on user-specific properties. For example, the user may provide controller 202 with head measurements, known hearing difficulties, age, sex, etc., or any other baseline characteristics that are user-specific. In some embodiments, hearing difficulty identifier 504 is configured to adjust its operation (e.g., use a different model, mine or search for different words/phrases, etc.) based on the baseline user-specific characteristics. In some embodiments, hearing difficulty identifier 504 performs (e.g., periodically) a selection process to identify which model or which set of phrases/words to search the text data for based on any of the environmental condition data and/or the baseline user-specific characteristics. In some embodiments, the baseline user-specific characteristics are provided to controller 202 and hearing difficulty identifier 504 by the user, or are obtained using appropriate sensors. In some embodiments, the baseline user-specific characteristics are only obtained, provided, or used if the user opts-in to allow controller 202 to obtain, receive, and use such data.

Referring still to FIG. 4, hearing assessment manager 500 includes environmental condition manager 506 which is configured to receive the audio signal(s) or audio data from audio capture device(s) 206, according to some embodiments. In some embodiments, environmental condition manager 506 is configured to analyze, process, or use the audio signal(s) to determine environmental condition data. In some embodiments, the environmental condition data includes an estimation of background noise (e.g., an amplitude in decibels). For example, environmental condition manager 506 may be configured to detect the amplitude of the background noise and can provide the environmental condition data to database manager 508.

Hearing difficulty identifier 504 can mine the text data for indications of hearing difficulty (and/or hearing ability) and provide hearing difficulty indications to database manager 508. In some embodiments, hearing difficulty identifier 504 provides the hearing difficulty indications (and/or the hearing ability indications) to database manager 508 in real-time (e.g., as the audio signals(s) are currently being obtained by transcription manager 502).

Database manager 508 receives the text data from transcription manager 502, hearing difficulty indications (and/or hearing ability indications) from hearing difficulty identifier 504, environmental condition data from environmental condition manager 506, and the audio signal(s) from audio capture device(s) 206, according to some embodiments. In some embodiments, database manager 508 is configured to log events of hearing difficulty in database 510. Database manager 508 can also be configured to log or store audio signal(s) obtained from audio capture device(s) 206 in database 510. Database manager 508 may log hearing difficulty events in database 510 with associated text data, environmental condition data, and the hearing difficulty indication. For example, the hearing difficulty indication may be a binary variable A such that A=0 or A=False to indicate that the user is having difficulty hearing (e.g., is unable to hear properly) or A=1 or A=True to indicate that the user is not having difficulty hearing (e.g., that the user is able to hear properly). Likewise, the hearing difficulty indication A may be A=1 or A=True to indicate that a hearing difficulty event has occurred or A=0 or A=False to indicate that a hearing difficulty event has not occurred. In some embodiments, database manager 508 also logs events or occurrences where the user is able to hear (i.e., when a hearing difficulty event does not occur). For example, hearing difficulty identifier 504 can also be configured to use the text data to search or mine for indications of hearing ability (e.g., particular spoken words, phrases, etc., that indicate the user is able to hear properly), and database manager 508 may log environmental conditions, and the text data preceding the hearing ability event, occurrence, or indication.

The log entries that are recorded in database 510 by database manager 508 can also include the text data (e.g., the phonemes, spoken words, phrases, etc.) and the environmental condition data preceding or associated with the hearing difficulty event (e.g., an amount of background noise in decibels associated with the hearing difficulty event). Database manager 508 can also write log entries to database 510 for events or text data that is not associated with a hearing difficulty event. For example, database manager 508 may log events, data entries, etc., including the hearing difficulty indication, the text data, and the environmental condition data for times when the user can hear properly. Advantageously, including hearing difficulty indications, text data, and environmental condition data in the hearing data stored in the database 510 facilitates generating a model, an audiogram, etc., for the user that is generated or trained based on conditions that are associated with the user being able to hear properly. This can improve the accuracy of the model or the audiogram. In some embodiments, database manager 508 is configured to write log events to database 510 over time to create training data, empirical data, hearing data, etc. In some embodiments, database manager 508 is configured to retrieve or read the hearing data from database 510 in response to a request and can provide the hearing data to hearing profile manager 600 (shown in FIG. 3) or to cloud computing system 204 or to ranking manager 512.

In some embodiments, the entries of database 510 are aggregated over time. For example, hearing assessment manager 500 may perform its functionality to generate the hearing data over a training time period. In some embodiments, hearing assessment manager 500 operates even when hearing enhancement manager 700, or the various other components of controller 202 operate, to update, adjust, improve, increase the size of, etc., the hearing data. In this way, hearing assessment manager 500 may initially operate over the training time period to generate baseline hearing data but may continually or intermittently operate thereafter to improve the hearing data (e.g., obtain additional log events or data entries for the database 510, overwrite entries in the hearing data, etc.).

Referring still to FIG. 4, database manager 508 can also provide the hearing data to ranking manager 512. Ranking manager 512 can also receive population hearing data (e.g., hearing data generated by controllers 202 of other sub-system 200) from cloud computing system 204 or from other sub-systems 200. In some embodiments, the hearing data received from hearing assessment manager 500 is for the particular user of sub-system 200. In some embodiments, ranking manager 512 is configured to use the hearing data of the particular user associated with the hearing assessment manager 500 (e.g., a user of sub-system 200) as well as population hearing data received from other sub-systems 200 or from cloud computing system 204 to generate, determine, output, etc., a user ranking. In some embodiments, the user ranking quantitatively defines how well the user is able to hear using the hearing data and the population hearing data. For example, the ranking may indicate, compared to the population of users, how well or how poorly the user can hear. In some embodiments, ranking manager 512 uses the hearing data from each of the other users (e.g., the population hearing data) and the hearing data of the particular user to identify a frequency of hearing difficulty events.

In some embodiments, ranking manager 512 is configured to receive a user audiogram or a hearing profile for the particular user from hearing profile manager 600. Ranking manager 512 can also be configured to obtain, receive, or request user audiograms or hearing profiles of other users in the population from cloud computing system 204 and/or from other sub-systems 200. In some embodiments, ranking manager 512 is configured to use the user audiogram and the population audiograms (e.g., the audiograms of different users) to determine a ranking for the particular user (i.e., a user ranking). In some embodiments, for example, ranking manager 512 uses the population audiograms to identify an average hearing ability for an individual across various frequencies. Ranking manager 512 may compare the particular user's audiogram to the average audiogram or the average hearing ability across the various frequencies to determine if the user has above or below average hearing abilities.

In some embodiments, ranking manager 512 is configured to use a known or predetermined model in addition to the user audiogram to determine if the user suffers from hearing difficulty (e.g., if the user has below average or below normal hearing abilities). For example, ranking manager 512 may compare the particular user's audiogram to a baseline audiogram to identify if the user suffers from any hearing difficulty across different frequencies. In some embodiments, the baseline audiogram that is used by ranking manager 512 to determine if the user suffers from hearing difficulty is selected based on sex, age, etc., of the user. For example, if the user has an age of 25, ranking manager 512 can select a baseline audiogram that indicates normal hearing abilities for a 25 year old (or for a range of ages that span across the age of 25) and may compare the particular user's audiogram to the baseline audiogram that is selected, obtained, or determined for the particular user (e.g., based on age, sex, etc.). In this way, the determination of whether or not the user suffers from hearing difficulty may be tailored to the specific user.

In some embodiments, ranking manager 512 is also configured to determine if the user suffers from hearing difficulty or hearing loss across particular frequencies, as well as a magnitude of hearing loss that the user experiences across the particular frequencies. For example, ranking manager 512 may determine (e.g., by comparing the user's audiogram to a corresponding baseline audiogram, by comparing the user's audiogram to the population audiograms, by comparing the user's audiogram to an average audiogram obtained using the population audiograms, etc.) that the user has normal hearing ability across a frequency of 250 to 500 Hz, but suffers from hearing loss across 2000 to 4000 Hz (e.g., the user is able to hear lower frequency sounds, but has difficulty hearing higher frequency sounds). In some embodiments, ranking manager 512 is configured to determine a difference or a magnitude of hearing loss between the baseline audiogram and the particular user's audiogram at multiple frequencies. For example, ranking manager 512 can determine a difference between the particular user's audiogram and the baseline audiogram for 100, 200, 300, . . . , 8000, Hz frequencies, or for any predetermined various frequency values. In some embodiments, ranking manager 512 determines an average hearing ability of the user across various frequency bands (e.g., across a 250 Hz to 500 Hz frequency band, a 500 Hz to 1000 Hz frequency band, a 2000 Hz to 4000 Hz frequency band, and a 4000 Hz to 8000 Hz frequency band) and compares the average hearing ability of the user to a corresponding hearing ability of a typical individual (e.g., a healthy or normal individual with healthy hearing abilities) to determine a difference between the particular user's hearing abilities and healthy or normal hearing abilities for each of the frequency bands.

Ranking manager 512 can output any of the user ranking, the user's hearing ability relative to a population, an average user's hearing ability, a healthy individual's hearing ability, etc., to hearing enhancement manager 700, or cloud computing system 204. In some embodiments, ranking manager 512 is configured to output the user audiogram or any of the analysis results of the user audiogram (e.g., any of the analysis, determinations, calculations, etc., performed by ranking manager 512 using any of the user audiogram, the population audiograms, the user's hearing data, the population hearing data, etc.) to hearing enhancement manager 700. In some embodiments, ranking manager 512 is configured to analyze the user audiogram to determine if the user suffers from hearing difficulty across any frequency ranges. In some embodiments, ranking manager 512 is configured to provide a notification, a message, etc., of the user hearing difficulty to the user. For example, ranking manager 512 can provide a notification (e.g., a visual notification, an aural notification, a combination thereof, etc.) that the user suffers from hearing difficulty of a particular magnitude across various frequency bands. In some embodiments, ranking manager 512 is configured to provide the notification, or generate a report for the user in response to receiving a user request. In some embodiments, ranking manager 512 is configured to operate a visual alert device (e.g., a display screen, a head wearable or head mounted display, etc.) and/or an aural alert device (e.g., a speaker, a wearable headset, etc.) to provide the visual and/or aural notification. For example, ranking manager 512 may provide a notification and/or a user ranking to user interface 210 which may include a display screen configured to provide, display, etc., imagery, text data, etc., to the user.

Hearing Profile Manager

Figure 5:
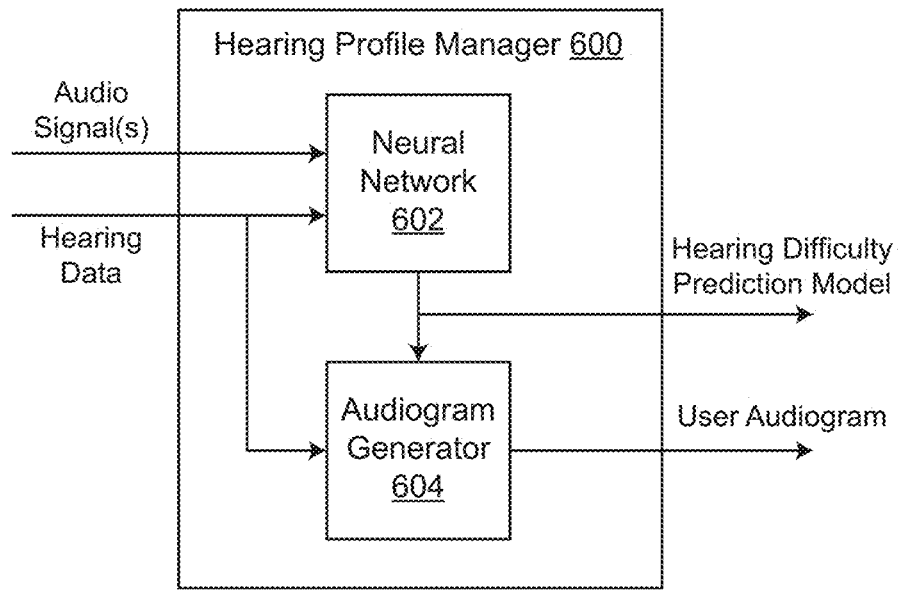
FIG. 5 is a block diagram of a hearing profile manager of the controller of FIG. 3, according to some embodiments.

Referring particularly to FIG. 5, hearing profile manager 600 is shown in greater detail, according to some embodiments. In some embodiments, hearing profile manager 600 is configured to receive the hearing data (e.g., from hearing assessment manager 500) and output the user audiogram and/or a hearing difficulty prediction model. In some embodiments, hearing profile manager 600 is configured to receive the particular user's hearing data from database manager 508 (shown in FIG. 5) and/or population data from cloud computing system 204 and/or from the other subsystem 200. Hearing profile manager 600 may use the hearing data obtained from database manager 508 and/or cloud computing system 204 to generate the hearing difficulty prediction model and the user audiogram.

Referring still to FIG. 5, hearing profile manager 600 includes a neural network, a machine learning model, etc., shown as neural network 602, and an audiogram generator 604. Neural network 602 is configured to receive the hearing data from database manager 508 of hearing assessment manager 500. In some embodiments, neural network 602 uses the aggregated hearing data to generate a personalized prediction model or a hearing difficulty prediction model. Neural network 602 can use the hearing data as training data for generating the hearing difficulty prediction model. In some embodiments, neural network 602 is configured to use the indications of hearing difficulty, the text data, and the environmental condition data to train the neural network 602. For example, the neural network 602 may use the indications of hearing difficulty, A, as the output of a model $f_{model}$, the text data (referred herein as $Data_{text}$), the audio signal(s) obtained from audio capture device(s) 206 (referred herein as $Data_{audio}$), and/or the environmental condition data (referred herein as $Env_{cond}$) as inputs to the model $f_{model}$. Neural network 602 is configured to predict the model $f_{model}$ that outputs or predicts indications of hearing difficulty as a function of (or given inputs of) the environmental condition data $Env_{cond}$ and the text data $Data_{text}$ (and/or audio data $Data_{audio}$) as shown below:

$$A = f_{model}(Env_{cond}, Data_{text}, Data_{audio}) \quad (1)$$

according to some embodiments. In some embodiments, the audio signal(s) or audio data obtained from audio capture device(s) 206 are used as an input to the model $f_{model}$ in combination with the text data $Data_{text}$ or without using the text data $Data_{text}$.

For example, neural network 602 is configured to predict the model $f_{model}$ that outputs or predicts indications of hearing difficulty as a function of the audio data $Data_{audio}$:

$$A = f_{model}(Data_{audio}) \quad (2)$$

according to some embodiments.

In some embodiments, the text data $Data_{text}$ includes one or more words that are generated during the voice recognition performed by transcription manager 502. For example, the text data $Data_{text}$ may include n number of words $w_1$ (e.g., phrases, sentences, etc.):

$$Data_{text} = [w_1 \ w_2 \ \ldots \ w_n] \quad (3)$$

as shown in Equation (3) above. In some embodiments, the number n of words $w_1$ is a predetermined number. In some embodiments, the number n of words is less than or equal to a predetermined amount. In some embodiments, the text data $Data_{text}$ is a complete sentence (e.g., in a user's conversation) and the number n of words $w_1$ varies based on the length of the sentences.

In some embodiments, each word $w_1$ includes multiple phonemes. For example, the first word $w_1$ may have $k_1$ number of phonemes, while the second word $w_2$ may have $k_2$ number of phonemes:

$$w_1 = [ph_{1,1} \ ph_{1,2} \ \ldots \ ph_{1,k_1}] \quad (4)$$

$$w_2 = [ph_{2,1} \ ph_{2,2} \ \ldots \ ph_{2,k_2}] \quad (5)$$

according to some embodiments. An arbitrary word $w_i$ has $k_i$ number of phonemes as shown in Equation (6) below:

$$w_i = [ph_{i,1} \ ph_{i,2} \ \ldots \ ph_{i,k_i}] \quad (6)$$

according to some embodiments.

In some embodiments, each phoneme ph is associated with a corresponding audio frequency f. For example, hearing profile manager 600 can be configured to convert each phoneme of any of the words w of the text data $Data_{text}$ of the hearing data to frequencies for training neural network 602. In some embodiments, neural network 602 uses the individual words, phonemes, or frequencies as inputs to the model $f_{model}$ during training so that the model $f_{model}$ can use particular words, phonemes, or frequencies to predict hearing difficulties A.

In other embodiments, the audio data $Data_{audio}$ is used directly as an input for the model $f_{model}$ to predict the hearing difficulties A (and/or to predict if the user will be able to hear particular audio data). In some embodiments, the neural network 602 is trained to generate the model $f_{model}$ that predicts hearing difficulties A given audio data $Data_{audio}$ input.

In some embodiments, neural network 602 uses weakly supervised learning to generate, train, define, construct, etc., the model $f_{model}$. In some embodiments, the model $f_{model}$ is a personalized hearing model for the user associated with hearing profile manager 600. For example, the model $f_{model}$ may predict hearing difficulties for the particular user given various text data inputs and environmental conditions. In this way, the model $f_{model}$ is personalized or tailored for the individual user and can be used to quantify the user's hearing ability across various frequencies.

In some embodiments, neural network 602 is configured to output the model $f_{model}$ to audiogram generator 604 and/or to cloud computing system 204. In some embodiments, audiogram generator 604 is configured to receive the model $f_{model}$ (i.e., the hearing difficulty prediction model) and uses the model $f_{model}$ to generate an audiogram for the user. For example, audiogram generator 604 can use weakly supervised learning to generate the user audiogram based on the model $f_{model}$. In some embodiments, audiogram generator 604 uses a known mapping or relationship between specific phonemes or frequencies and hearing difficulty for the user (e.g., as represented by the model $f_{model}$) to construct the audiogram or a hearing profile. Audiogram generator 604 can also use the hearing data directly to generate, estimate, define, output, determine, etc., the audiogram (i.e., the user audiogram). In some embodiments, the audiogram is generated based on the personalized model $f_{model}$ for the particular user (e.g., the user from which the hearing data was obtained) so that the audiogram quantifies the particular user's hearing ability across various frequencies.

Figure 6:
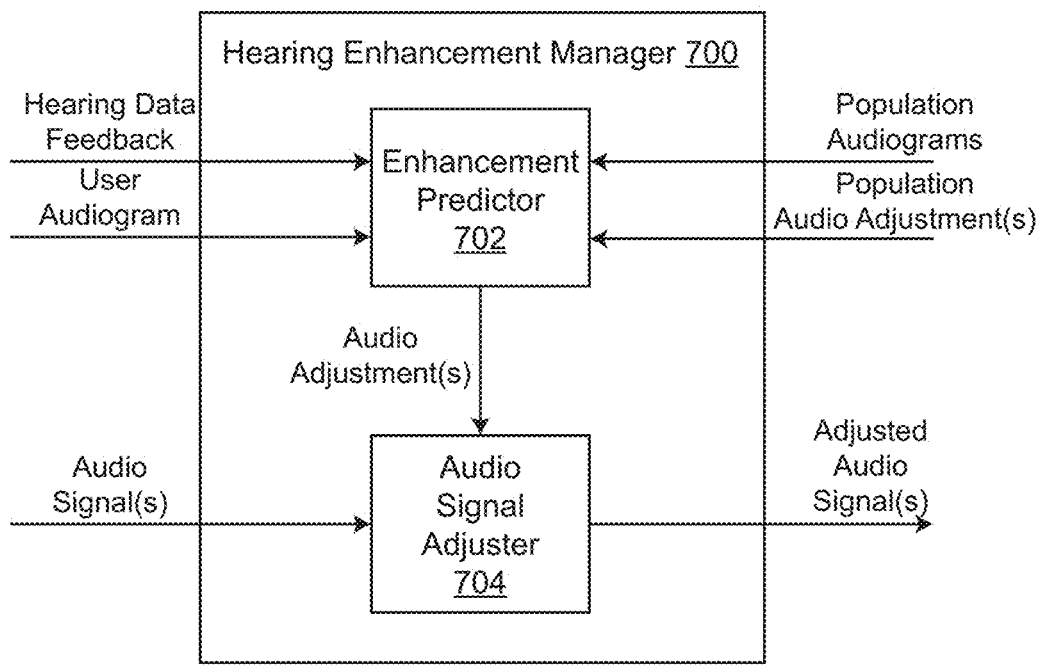
FIG. 6 is a block diagram of a hearing enhancement manager of the controller of FIG. 3, according to some embodiments.

In some embodiments, audiogram generator 604 outputs the user audiogram to any of hearing assessment manager 500, hearing enhancement manager 700, and/or cloud computing system 204. Specifically, audiogram generator 604 can output the user audiogram to ranking manager 512 of hearing assessment manager 500, or enhancement predictor 702 of hearing enhancement manager 700 (as shown in FIG. 6 and described in greater detail below). The audiogram for the particular user can be used by any of the portions of controller 202 for their respective functionality as described herein.

Example Audiogram

Figure 8:
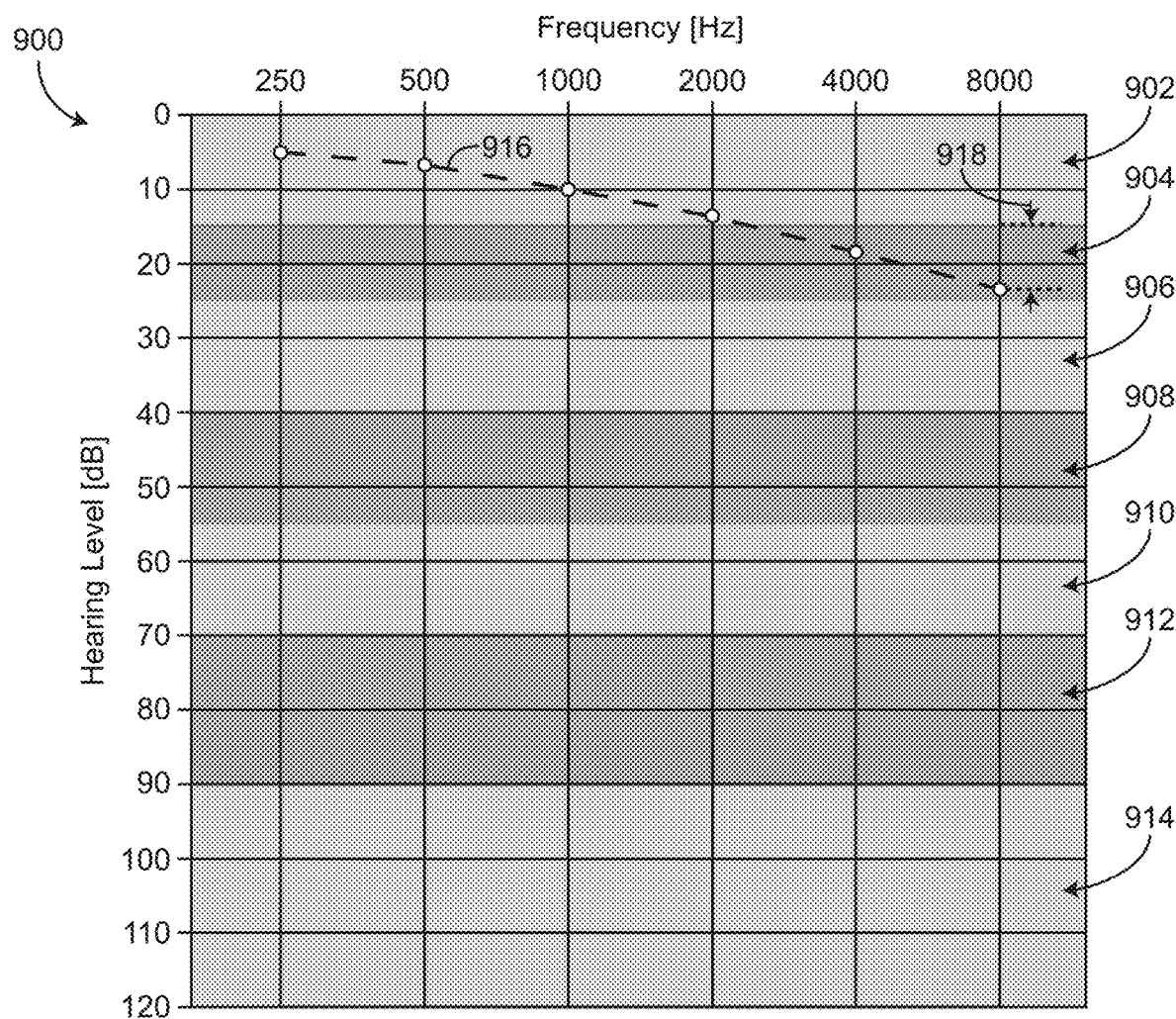
FIG. 8 is a graph of an audiogram that may be generated by the sub-system of FIG. 3, according to some embodiments.

Referring particularly to FIG. 8, graph 900 shows an example audiogram 916 that may be generated by audiogram generator 604, according to some embodiments. Graph 900 includes an X-axis demonstrating frequency in Hertz, with respect to a Y-axis that demonstrates the user's hearing level in decibels. Graph 900 ranges from 250 Hz to 8000 Hz, according to some embodiments. In some embodiments, graph 900 ranges from a frequency less than 250 Hz or to a frequency greater than 8000 Hz. Graph 900 includes a normal hearing region 902 from a hearing level of 0-15 dB, a slight hearing loss region 904 from a hearing level of 15-25 dB, a mild hearing loss region 906, from a hearing level of 25-40 dB, a moderate hearing loss region 908 from a hearing level of 40-55 dB, a moderately-severe hearing loss region 910 from a hearing level of 55-70 dB, a severe hearing loss region 912 from a hearing level of 70-90 dB, and a profound hearing loss region 914 from a hearing level of 90 dB or greater. It should be understood that the various hearing loss regions described herein are illustrative and that regions of hearing loss may be defined differently.

Graph 900 includes example audiogram 916 that spans from 250 Hz to 8000 Hz. As shown in FIG. 8, audiogram 916 is within the normal hearing region 902 from approximately 250 Hz to 2000 Hz. Above 2000 Hz, audiogram 916 lies within the slight hearing loss region 904. This may indicate that the user has difficulty hearing higher frequency sounds (e.g., sounds above 2000 Hz). In some embodiments, controller 202 can use the audiogram 916 to identify certain frequencies or ranges of frequencies that the user has difficulty hearing, and may adjust sound output of a sound producing device for these particular frequencies to improve the user's ability to hear properly. In some embodiments, controller 202 can provide the user with an indication or notification that the user suffers from slight, mild, moderate, moderately-severe, severe, or profound hearing loss across various frequencies.

Hearing Enhancement Manager

Referring particularly to FIG. 6, hearing enhancement manager 700 is shown in greater detail, according to some embodiments. In some embodiments, hearing enhancement manager 700 includes an enhancement predictor 702 and an audio signal adjuster 704. In some embodiments, enhancement predictor 702 is configured to receive the user audiogram (e.g., from audiogram generator 604) and population audiograms from cloud computing system 204. In some embodiments, enhancement predictor 702 is also configured to receive real-time hearing data, shown as hearing data feedback.

In some embodiments, enhancement predictor 702 is configured to use the audiogram to generate, determine, estimate, etc., hearing enhancements or audio adjustments. Enhancement predictor 702 may provide the audio adjustments to audio signal adjuster 704. In some embodiments, the audio adjustment(s) indicate an amount to increase output audio that is provided to the user for particular frequencies. For example, enhancement predictor 702 can use the user audiogram to identify that the user may benefit from hearing enhancements or audio adjustments for high frequency sounds.

Referring particularly to FIGS. 6 and 8, enhancement predictor 702 may estimate, calculate, determine, obtain, etc., a difference 918 between the audiogram 916 and a reference audiogram, or a particular hearing level. For example, enhancement predictor 702 can calculate an average difference between the audiogram 916 and a baseline hearing level (e.g., at the transition between the normal hearing region 902 and the slight hearing loss region 904, at 0 dB hearing level, etc.) for multiple frequencies (e.g., for various frequencies from 250 Hz to 8000 Hz). In some embodiments, enhancement predictor 702 obtains or receives population audiograms from other users in the population, and calculates an average audiogram. In some embodiments, enhancement predictor 702 determines the difference 918 in the hearing level between the particular user's audiogram 916 and the average audiogram or the baseline audiogram that is obtained by averaging the population audiograms. In some embodiments, the baseline hearing level or the baseline audiogram is selected by or generated by enhancement predictor 702 based on an age of the particular user, a sex of the particular user, etc. In this way enhancement predictor 702 can identify if the user has hearing loss for their particular age and sex. In some embodiments, enhancement predictor 702 is configured to estimate the difference 918 between the baseline hearing level or the baseline audiogram and the particular user's audiogram 916 at frequencies where it is identified that the particular user has hearing difficulty (e.g., across portions of audiogram 916 that lie outside of the normal hearing region 902). In this way, enhancement predictor 702 can identify a magnitude of hearing loss for the particular user across particular frequency ranges.

Referring again to FIG. 6, in some embodiments, enhancement predictor 702 uses a predetermined model, set of rules, equations, etc., to identify audio adjustments for the particular user based on the user's audiogram. The audio adjustment(s) can include frequency adjustments, amplification adjustments, or any other audio adjustment(s) for an audio signal. In some embodiments, the audio adjustment(s) are specific for particular frequency ranges. For example, enhancement predictor 702 can identify the particular user has severe hearing loss for high frequency sounds (based on the user's audiogram), and may determine audio adjustment(s) for high frequency sounds to improve the user's ability to hear. In some embodiments, enhancement predictor 702 uses a predetermined or pre-trained model to determine the audio adjustment(s) for the particular user (e.g., based on the user's audiogram). In some embodiments, enhancement predictor 702 is configured to train the model, adjust the model, adjust parameters of the model, etc., based on hearing data that is obtained after the audio adjustment(s) are implemented. For example, hearing enhancement manager 700, hearing profile manager 600, and hearing assessment manager 500 may operate initially to develop an initial model $f_{model}$, an initial audiogram for the user, and initial audio adjustment(s) for the user. However, after the initial model $f_{model}$ has been developed, hearing assessment manager 500, hearing profile manager 600, and hearing enhancement manager 700 may continue to perform their functionality to verify that the audio adjustment(s) and/or the initial model $f_{model}$ are accurate and/or provide sufficient hearing enhancements for the user.

In some embodiments, enhancement predictor 702 is configured to receive population audiograms and corresponding population audio adjustments from cloud computing system 204. Enhancement predictor 702 may also receive hearing data from cloud computing system 204 relating to different users across the population of sub-systems 200.

Hearing Assessment and Enhancement Process

Figure 7:
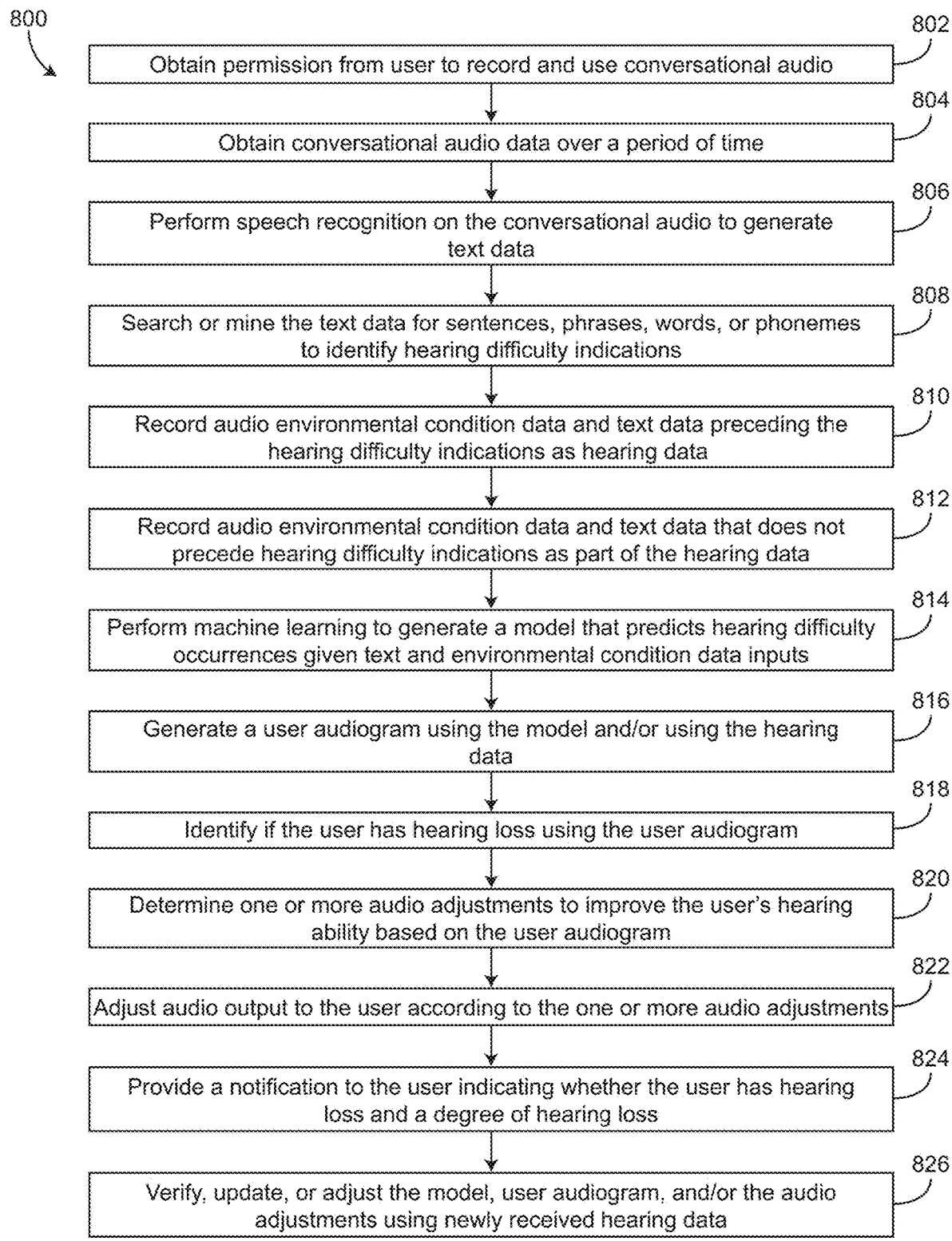
FIG. 7 is a flow diagram of a process for assessing a user's hearing abilities and adjusting audio output for the user to reduce hearing difficulty, according to some embodiments.

Referring particularly to FIG. 7, a process 800 for assessing a user's hearing, and improving audio output of a wearable audio device to account for user hearing difficulty is shown, according to some embodiments. In some embodiments, process 800 includes steps 802-826. In some embodiments, process 800 is performed by any of sub-systems 200. In some embodiments, process 800 is performed by controller 202, cloud computing system 204, audio capture device(s) 206, and audio output device(s) 208. In some embodiments, process 800 is performed to passively assess the user's hearing, and to determine if the user suffers from hearing loss across various frequency ranges (e.g., frequency bins). In some embodiments, process 800 is performed to determine one or more audio adjustments that reduce a frequency or likelihood that the user is unable to hear a particular sound or a particular spoken phrase. In some embodiments, process 800 can be performed passively to constantly update the various models, adjustments, enhancements, etc. In some embodiments, process 800 includes receiving data from other sub-systems that perform a same or similar process to train across a population.

Process 800 includes obtaining permission from a user to record and use conversational audio (step 802), according to some embodiments. In some embodiments, step 802 can be performed by providing the user with a request or an option to opt-in for passive hearing enhancement and assessment. In some embodiments, the request or the option includes an indication that conversational audio will be collected and analyzed if the user selects to opt-in for the passive hearing assessment and improvements. In some embodiments, the request or option also includes an indication or message that various models, hearing profiles, audiograms, audio adjustments, etc., that are tailored specifically for the user may be uploaded to a cloud computing system to improve the accuracy of other user's models, hearing profiles, audiograms, audio adjustments, etc. In some embodiments, process 800 proceeds to step 804 only if the user opts-in for passive hearing assessment and enhancement.

Process 800 includes obtaining conversational audio of the user over a time period (step 804), according to some embodiments. In some embodiments, step 804 is performed by hearing assessment manager 500 and audio capture device(s) 206. In some embodiments, step 804 is only performed if the user opts-in to allow controller 202 to collect, analyze, store, etc., audio data (e.g., conversational audio data) for the passive hearing assessment and enhancement features or functionality. In some embodiments, the conversational audio is obtained from a microphone on a head wearable device (e.g., an augmented reality device, a virtual reality device, a mixed reality device, etc.), a microphone on a smartphone or personal computer device, etc. In some embodiments, the conversational audio data is obtained from multiple microphones. In some embodiments, the conversational audio data is obtained over a training period or an initial period for an initial implementation of process 800. In some embodiments, the conversational audio data is obtained even after an initial period over which an initial model, audiogram, hearing profile, audio adjustments, etc., are determined.

Process 800 includes performing speech or voice recognition on the conversational audio data to generate text data, conversational data, transcription data, etc., (step 806), according to some embodiments. In some embodiments, step 806 is performed using a speech or voice recognition engine. For example, step 806 can be performed by hearing assessment manager 500 of controller 202, or more particularly, by transcription manager 502. In some embodiments, step 806 is performed using a variety of techniques to identify phonemes, spoken words, phrases, etc., in the conversational audio data, and generate textual information or data of the detected phonemes, spoken words, phrases, etc. In some embodiments, step 806 includes identifying different speakers in the conversational audio data.

Process 800 includes searching or mining the text data for sentences, phrases, words, or phonemes that indicate hearing difficulty (step 808), according to some embodiments. In some embodiments, step 808 is performed by hearing assessment manager 500, or more specifically, by hearing difficulty identifier 504. In some embodiments, the sentences, phrases, words, of phonemes are sentences, phrases, words, or phonemes that are known to indicate hearing difficulty. For example, a phrase that may indicate hearing difficulty may be "Could you repeat that?" or "What did you say?". In some embodiments, the phrases that indicate hearing difficulty are stored in a database and used by hearing difficulty identifier 504 to determine occurrences or events where the user has difficulty hearing. In some embodiments, hearing difficulty identifier 504 is configured to define a variable A that indicates whether or not a hearing difficulty event has occurred. For example, the variable A may be a binary variable (e.g., either 1 or 0) indicating whether or not a hearing difficulty even has occurred.

Process 800 includes recording audio environmental condition data and text data preceding the hearing difficulty indications as part of the hearing data (step 810), according to some embodiments. In some embodiments, step 810 is performed by hearing assessment manager 500, or more particularly by database manager 508 and database 510. For example, database manager 508 may receive values of the variable A indicating whether or not a hearing difficulty event has occurred. In some embodiments, database manager 508 is configured to obtain values of the variable A over time and also obtain values of the text data and the environmental condition data from transcription manager 502 and environmental condition manager 506, respectively. Database manager 508 can record data entries of the text data, the environmental condition data, audio data, and the hearing difficulty indication, and store the entries in database 510. In some embodiments, database manager 508 is configured to store the data entries in database 510 to generate training data, or hearing data. The hearing data includes environmental conditions, text data, speech/audio data, and an indication of whether or not the particular environmental conditions, speech/audio data, and text data result in hearing difficulty for the user. In some embodiments, the hearing data is collected, generated, etc., by database manager 508 over a training time period and stored in database 510 for use (e.g., to generate a hearing profile, an audiogram, a prediction model, etc.). In some embodiments, database manager 508 is responsible for writing data entries to database 510 and for retrieving the data from database 510.

Process 800 includes recording audio environmental condition data and text data that does not precede hearing difficulty indications as part of the hearing data (step 812), according to some embodiments. In some embodiments, step 812 is similar to step 810 but for collecting data (e.g., text data, speech/audio data, and environmental condition data) that does not result in a hearing difficulty event. In some embodiments, step 812 is performed so that the hearing data also includes examples of or data corresponding to conditions when the user is able to hear properly. This can improve the hearing data, providing a wider range of conditions and giving a better representation of the user's hearing abilities.

Process 800 includes performing machine learning to generate a model that predicts hearing difficulty occurrences given text, speech/audio data, and environmental condition data inputs (step 814), according to some embodiments. In some embodiments, step 814 is performed by hearing profile manager 600, or more specifically, by neural network 602. In some embodiments, step 814 includes using the hearing data that is collected or generated in steps 810-812. The machine learning can be performed to generate a model that predicts whether or not a user will experience hearing difficulty (e.g., a value of the variable A) given environmental condition data inputs and text data inputs. In some embodiments, the machine learning uses consonant sounds, vowel sounds, phonemes, etc., of the words to identify particular frequencies, words, or sounds that the user has difficulty hearing. For example, the model generated by the machine learning may be the model $f_{model}$ as shown in Equation (1) and described in greater detail above.

Process 800 includes generating a user audiogram using the model and/or the hearing data (step 816), according to some embodiments. In some embodiments, step 816 is performed by audiogram generator 604. For example, audiogram generator 604 may receive the model $f_{model}$ generated in step 814 and estimate a user hearing profile or an audiogram for the user based on the model $f_{model}$. In some embodiments, the user hearing profile or the audiogram indicates a user's hearing ability across various frequencies.

Process 800 includes identifying if the user has hearing loss using the user audiogram (step 818), according to some embodiments. In some embodiments, step 818 is performed by hearing enhancement manager 700. In some embodiments, step 818 includes identifying if the user's audiogram is in any of a normal hearing region, a slight hearing loss region, a mild hearing loss region, a moderate hearing loss region, a moderately-severe hearing loss region, a severe hearing loss region, or a profound hearing loss region across various frequencies. For example, step 818 can include identifying one or more portions of the user's audiogram that are not within the normal hearing region, and determining that the user has difficulty hearing particular frequencies where the portions of the user's audiogram fall outside of the normal hearing region. In some embodiments, step 818 includes comparing the user's audiogram to a baseline audiogram that indicates normal hearing abilities. In some embodiments, the baseline audiogram is selected based on an age or sex of the user. In some embodiments, the baseline audiogram is an average audiogram of various users across a population. For example, controller 202 can obtain user audiograms from other users in the population (e.g., from cloud computing system 204), and may average, aggregate, etc., or otherwise define the baseline audiogram using the audiograms from the other users in the population. In this way, step 818 can include comparing the user's audiogram to other audiograms of the population. In some embodiments, step 818 is performed by ranking manager 512. For example, ranking manager 512 can rank the user's audiogram relative to other users' audiograms in the population (e.g., user audiograms determined by other sub-systems 200) to determine the user's hearing ability relative to other users in the population (e.g., to determine what percentile the user lies in with respect to hearing ability).

Process 800 includes determining one or more audio adjustments to improve the user's hearing ability based on the user audiogram (step 820), according to some embodiments. In some embodiments, step 820 is performed by enhancement predictor 702. Enhancement predictor 702 can use the user audiogram determined in step 816 to identify audio output adjustments that reduce a frequency or likelihood of a hearing difficulty occurrence. For example, step 820 may include identifying that the user has difficulty hearing high-frequency sounds or noises, and determining audio adjustments for high-frequency sounds or noises to improve the user's ability to hear the high-frequency sounds. In some embodiments, the audio adjustments include volume or sound output level adjustments for various frequencies that the user has difficulty hearing.

Process 800 includes adjusting audio output to the user according to the one or more audio adjustments (step 822), according to some embodiments. In some embodiments, step 822 is performed by hearing enhancement manager 700 and audio output device(s) 208. For example, the audio output to the user may be provided by head wearable speakers that are positioned proximate the user's ears and configured to provide sound waves to the user. In some embodiments, audio signal adjuster 704 is configured to receive the audio adjustment(s) from enhancement predictor 702 and use the audio adjustment(s) to change, modify, adjust, etc., received audio signal(s). In some embodiments, audio signal adjuster 704 receives audio signal(s) and uses the audio adjustment(s) to output adjusted audio signal(s). In some embodiments, audio signal adjuster 704 is configured to provide the adjusted audio signal(s) to audio output device(s) 208. In some embodiments, for example, audio output device(s) 208 are configured to receive the adjusted or modified audio signal(s) and use the adjusted audio signal(s) to output or provide sound waves to the user.

Process 800 includes providing a notification to the user indicating whether the user has hearing loss and a degree of hearing loss (step 824), according to some embodiments. In some embodiments, step 824 is performed by operating a visual and/or an aural alert device of the sub-system 200 to provide the notification to the user. For example, step 824 can include operating a display device of sub-system 200 to notify the user whether the user suffers from hearing loss. In some embodiments, the indication or notification provided to the user includes the degree of hearing loss that the user suffers. For example, the indication or notification can include the user's ranking relative to other users in the population, which of regions 902-914 the user's audiogram lies within at different frequencies, a hearing level difference between the user's audiogram and a normal hearing audiogram or a baseline audiogram (e.g., an audiogram of a user with average or healthy hearing abilities). In some embodiments, the notification also includes a graphical representation of the user's audiogram. For example, controller 202 may operate a display screen, a wearable display screen, a combiner, etc., of sub-system 200 to display the graphical representation of the user's audiogram. In some embodiments, the notification also includes a recommendation of whether or not the user should visit a hearing specialist.

Process 800 includes verifying, updating, or adjusting the model, user audiogram, and/or the audio adjustments using newly received hearing data (step 826), according to some embodiments. In some embodiments, step 826 includes re-performing steps 804-816 and 820 to update, adjust, verify, etc., any of the hearing data, the model, the user audiogram, and/or the audio adjustments. In some embodiments, step 826 is performed by the various portions of controller 202. For example, the newly received hearing data can be used to identify if the user is still having hearing difficulty even while sub-system 200 operates to implement the audio adjustment(s). In some embodiments, the newly received hearing data can be used to verify whether the audio adjustment(s) are beneficial or reduce a frequency of hearing difficulty events.

Population Wide Training

Referring again to FIG. 6, enhancement predictor 702 can be configured to learn, adapt, update, etc., across all users of the population (e.g., using data from all sub-systems 200 of the system 300). For example, enhancement predictor 702 can be configured to receive population audiograms and/or population audio adjustments from other sub-systems 200 in system 300. In some embodiments, enhancement predictor 702 is configured to use the population audiograms and the corresponding population audio adjustment(s) to determine the audio adjustment(s) for the particular user. For example, enhancement predictor 702 can compare the particular user's audiogram to various population audiograms, and determine similarities between the users audiograms. For example, enhancement predictor 702 may identify that the particular user suffers from hearing loss across a particular frequency range (e.g., from $f_1$ to $f_2$) and may identify other users in the population with similar hearing loss. In some embodiments, enhancement predictor 670 may use similar audio adjustments for the particular user as the other users with similar hearing loss.

In some embodiments, enhancement predictor 702 is configured to identify a magnitude of hearing loss across various frequencies using the particular user's audiogram. Enhancement predictor 702 can be configured to identify similar magnitudes of hearing loss across other users in the population (e.g., using the population audiograms), and identify the audio adjustment(s) used for the similar users. In some embodiments, enhancement predictor 702 uses machine learning, a neural network, an adaptive model, etc., to determine the audio adjustment(s) based on or using the user's audiogram. In some embodiments, enhancement predictor 702 is configured to use the population audiograms, the population audio adjustment(s), and/or population data (e.g., hearing data obtained from other sub-systems 200 of the population) to train the model. In this way, enhancement predictor 702, or more generally, hearing enhancement manager 700 may learn or train across all users of the population (or all users of the population that have opted-in for sharing their respective data).

Closed Loop Audio Enhancement Adjustments

Referring particularly to FIGS. 3 and 6, hearing enhancement manager 700 is configured to receive hearing data feedback from hearing assessment manager 500, and adjust the audio adjustment(s) based on the hearing data feedback. In some embodiments, hearing assessment manager 500 is configured to perform its respective functionality in real-time to generate the hearing data feedback. For example, hearing assessment manager 500 can operate in real-time to obtain audio signal(s) from audio capture device(s) 206, even after hearing enhancement manager 700 has performed its functionality to adjust the sounds output by audio output device(s) 208.

In some embodiments, enhancement predictor 702 uses the hearing data feedback to identify if a frequency of hearing difficulty events or hearing difficulty indications has decreased. In some embodiments, enhancement predictor 702 monitors the environmental conditions and/or text data of the hearing data feedback to identify conditions that would have previously resulted in hearing difficulty (e.g., before the audio adjustment(s) were implemented). If implementing the audio adjustment(s) results in decreased frequency or a decreased number of hearing difficulty events or hearing difficulty indications, enhancement predictor 702 may determine that the audio adjustment(s) are effective. If the user still suffers from hearing difficulty, enhancement predictor 702 may adjust the audio adjustments, and monitor the hearing data feedback to identify if the adjusted audio adjustment(s) are more effective. If the number or frequency of hearing difficulty events or hearing difficulty indications increases after the audio adjustment(s) are implemented, or after the audio adjustment(s) are adjusted, enhancement predictor 702 may determine that the audio adjustment(s) are ineffective or that the audio adjustment(s) should be changed, updated, adjusted, recalculated, etc.

In some embodiments, hearing enhancement manager 700 and hearing assessment manager 500 cooperatively function to evaluate, assess, etc., the audio adjustment(s) determined by enhancement predictor 702. In some embodiments, hearing enhancement manager 700 and hearing assessment manager 500 are configured to identify if the audio adjustment(s) improve the user's listening experience (e.g., decrease a number and/or frequency of hearing difficulty events). In some embodiments, hearing enhancement manager 700 and/or hearing assessment manager 500 are configured to monitor or track times at which the audio adjustment(s) are implemented, or when the audio adjustment(s) are changed. In this way, hearing enhancement manager 700 and hearing assessment manager 500 can identify, track, map, etc., particular audio adjustment(s) to identify the effectiveness of particular audio adjustment(s). In some embodiments, hearing enhancement manager 700 and/or hearing assessment manager 500 are configured to report, provide, etc., the particular audio adjustment(s) and their effectiveness or associated hearing data (in addition to the particular user's audiogram) to cloud computing system 204 so that other sub-systems 200 may use this data to determine audio adjustment(s) for their particular users.

In this way, hearing profile manager 600, hearing assessment manager 500, and hearing enhancement manager 700 can operate continuously in a closed-loop manner to provide continuous updates, adjustments, etc., for the adjusted audio signal(s). In some embodiments, hearing assessment manager 500 and hearing enhancement manager 700 operate cooperatively until controller 202 determines that additional audio adjustment(s) are not required.

System Functionality Diagram

Figure 9:
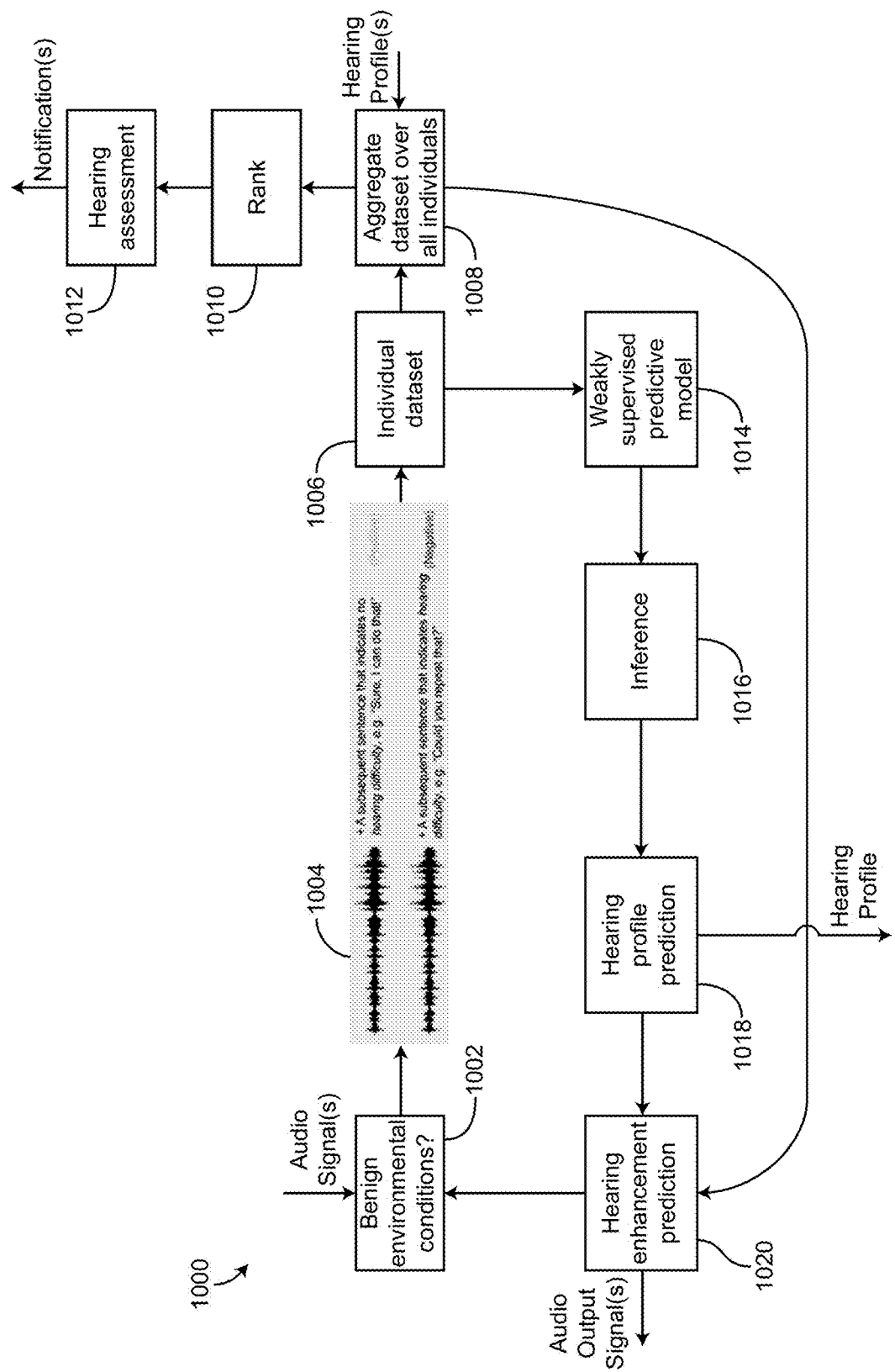
FIG. 9 is a diagram of a system for performing passive hearing assessment and hearing enhancement, according to some embodiments.

Referring particularly to FIG. 9, a block diagram of a system 1000 illustrates the functionality of the sub-system 200, according to some embodiments. Any of the functionality, techniques, or steps of system 1000 as described herein may be performed by controller 202. System 1000 includes a passive hearing assessment system 1012, a hearing profile characterization system 1018, and a continuous hearing enhancement system 1020, according to some embodiments.

System 1000 is configured to determine if the environmental conditions are sufficiently benign (at block 1002), according to some embodiments. In some embodiments, if the environmental conditions are sufficiently benign, system 1000 collects audio data and detects if the user has had difficulty hearing (e.g., by mining for particular words, phrases, etc.), shown as indication 1004. System 1000 can detect positive indications 1004 (e.g., indicating that the user can properly hear) or negative indications 1004 (e.g., indicating that the user cannot hear properly). In some embodiments, system 1000 uses the positive and/or negative indications 1004 to generate an individual dataset 1006. In some embodiments, the individual dataset 1006 is the same as or similar to the hearing data stored in database 510 as described in greater detail above with reference to FIG. 4.

System 1000 is configured to provide the individual dataset 1006 to a weakly supervised predictive model 1014, according to some embodiments. In some embodiments, the weakly supervised predictive model 1014 is configured to perform an inference 1016 or to output a model. The inference 1016, the weakly supervised predictive model 1014, and the individual dataset 1006 may all be portions of the hearing profile characterization system 1018, according to some embodiments.

Under predefined environment conditions that pose no hearing challenges to a person with nominal hearing, (e.g., low noise levels at block 1002), the passive hearing assessment system 1012 monitors one-on-one conversations, converts speech-to-text, and mines the text for words or phrases that indicate difficulty of hearing (e.g., "could you repeat that?"). Together with the environment conditions at the time, the spoken words or phrases that are not followed by indications of hearing difficulty are collected, stored, and marked as such, as well as the spoken words or phrases that are followed by indications of hearing difficulty in the individual dataset 1006. A database of environment conditions and spoken words or phrases with markings (labels) of hearing difficulty, or the lack of, aggregated over a period of time from many individuals can be used to generate a rank 1010 of all individuals in the population based on the environment conditions, the dialogue in the conversation, and the frequency of words or phrases that were followed by indications of hearing difficulty relative to those that were not followed by indications of hearing difficulty. The bottom ranked individuals likely suffer some degree of hearing difficulty and would benefit from hearing enhancements.

In some embodiments, the hearing profile characterization system 1018 is configured to use spoken words or phrases that were not followed by indications of hearing difficulty (positive) and those that were followed by indications of hearing difficulty (negative) for a single individual, aggregated over a period of time as described above to generate a prediction model. In some embodiments, the hearing profile characterization system 1018 trains a machine learning model to predict whether a word or a phrase would be a positive or negative hearing situation (e.g., the weakly supervised predictive model). This machine learning model is a personalized prediction model for a single user that models the hearing profile of this user, according to some embodiments. Using techniques from weakly supervised learning, a representation that correlates phonemes or frequencies with hearing difficulty is inferred and used to construct an individualized hearing profile (audiogram), according to some embodiments.

In some embodiments, the individualized hearing profile (audiogram) is used by the continuous hearing enhancement system 1020 to predict hearing enhancements. The passive hearing assessment system 1012 and the hearing profile characterization system 1018 are then used to evaluate the prediction from the continuous hearing enhancement system 1020, according to some embodiments. This closed loop continues until no further enhancement is required by the continuous hearing enhancement system 1020. In some embodiments, the continuous hearing enhancement system 1020 receives aggregated datasets 1008 over all individuals in the population and learns across all individuals in the population.

Opt-In Data Collection

In particular embodiments, the system 300 may have functionalities that may use, as inputs, personal or biometric information of a user for user-authentication or experience-personalization purposes. A user may opt to make use of these functionalities to enhance their experience on the online social network. As an example and not by way of limitation, a user may provide personal or biometric information to the system 300. The user's privacy settings may specify that such information may be used only for particular processes, such as authentication, and further specify that such information may not be shared with any third-party system or used for other processes or applications associated with the system 300. As another example and not by way of limitation, the system 300 or sub-system 200 may provide a functionality for a user to provide voice-print recordings to the online social network. As an example and not by way of limitation, if a user wishes to utilize this function of the online social network, the user may provide a voice recording of his or her own voice to provide a status update on the online social network. The recording of the voice-input may be compared to a voice print of the user to determine what words were spoken by the user. The user's privacy setting may specify that such voice recording may be used only for voice-input purposes (e.g., to authenticate the user, to send voice messages, to improve voice recognition in order to use voice-operated features of the online social network), and further specify that such voice recording may not be shared with any third-party system or used by other processes or applications associated with the system 300 or sub-system 200. As another example and not by way of limitation, the system 300 or sub-system 200 may provide a functionality for a user to provide a reference image (e.g., a facial profile, a retinal scan) to the online social network. The online social network may compare the reference image against a later-received image input (e.g., to authenticate the user, to tag the user in photos). The user's privacy setting may specify that such voice recording may be used only for a limited purpose (e.g., authentication, tagging the user in photos), and further specify that such voice recording may not be shared with any third-party system or used by other processes or applications associated with the system 300 or the sub-system 200.

In particular embodiments, changes to privacy settings may take effect retroactively, affecting the visibility of objects and content shared prior to the change. As an example and not by way of limitation, a first user may share a first image and specify that the first image is to be public to all other users. At a later time, the first user may specify that any images shared by the first user should be made visible only to a first user group. The system 300 or sub-system 200 may determine that this privacy setting also applies to the first image and make the first image visible only to the first user group. In particular embodiments, the change in privacy settings may take effect only going forward. Continuing the example above, if the first user changes privacy settings and then shares a second image, the second image may be visible only to the first user group, but the first image may remain visible to all users. In particular embodiments, in response to a user action to change a privacy setting, the system 300 or sub-system 200 may further prompt the user to indicate whether the user wants to apply the changes to the privacy setting retroactively. In particular embodiments, a user change to privacy settings may be a one-off change specific to one object. In particular embodiments, a user change to privacy may be a global change for all objects associated with the user.

In particular embodiments, the system 300 or sub-system 200 may determine that a first user may want to change one or more privacy settings in response to a trigger action associated with the first user. The trigger action may be any suitable action on the online social network. As an example and not by way of limitation, a trigger action may be a change in the relationship between a first and second user of the online social network (e.g., "un-friending" a user, changing the relationship status between the users). In particular embodiments, upon determining that a trigger action has occurred, the system 300 or sub-system 200 may prompt the first user to change the privacy settings regarding the visibility of objects associated with the first user. The prompt may redirect the first user to a workflow process for editing privacy settings with respect to one or more entities associated with the trigger action. The privacy settings associated with the first user may be changed only in response to an explicit input from the first user, and may not be changed without the approval of the first user. As an example and not by way of limitation, the workflow process may include providing the first user with the current privacy settings with respect to the second user or to a group of users (e.g., un-tagging the first user or second user from particular objects, changing the visibility of particular objects with respect to the second user or group of users), and receiving an indication from the first user to change the privacy settings based on any of the methods described herein, or to keep the existing privacy settings.

In particular embodiments, a user may need to provide verification of a privacy setting before allowing the user to perform particular actions on the online social network, or to provide verification before changing a particular privacy setting. When performing particular actions or changing a particular privacy setting, a prompt may be presented to the user to remind the user of his or her current privacy settings and to ask the user to verify the privacy settings with respect to the particular action. Furthermore, a user may need to provide confirmation, double-confirmation, authentication, or other suitable types of verification before proceeding with the particular action, and the action may not be complete until such verification is provided. As an example and not by way of limitation, a user's default privacy settings may indicate that a person's relationship status is visible to all users (i.e., "public"). However, if the user changes his or her relationship status, the system 300 or sub-system 200 may determine that such action may be sensitive and may prompt the user to confirm that his or her relationship status should remain public before proceeding. As another example and not by way of limitation, a user's privacy settings may specify that the user's posts are visible only to friends of the user. However, if the user changes the privacy setting for his or her posts to being public, the system 300 or sub-system 200 may prompt the user with a reminder of the user's current privacy settings of posts being visible only to friends, and a warning that this change will make all of the user's past posts visible to the public. The user may then be required to provide a second verification, input authentication credentials, or provide other types of verification before proceeding with the change in privacy settings. In particular embodiments, a user may need to provide verification of a privacy setting on a periodic basis. A prompt or reminder may be periodically sent to the user based either on time elapsed or a number of user actions. As an example and not by way of limitation, the system 300 or sub-system 200 may send a reminder to the user to confirm his or her privacy settings every six months or after every ten photo posts. In particular embodiments, privacy settings may also allow users to control access to the objects or information on a per-request basis. As an example and not by way of limitation, the system 300 or sub-system 200 may notify the user whenever a third-party system attempts to access information associated with the user, and require the user to provide verification that access should be allowed before proceeding.

Configuration of Illustrative Embodiments

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Systems and methods described herein may be embodied in other specific forms without departing from the characteristics thereof. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. The orientation of various elements may differ according to other exemplary embodiments, and that such variations are intended to be encompassed by the present disclosure.

What is claimed is:

1. An audio system for user hearing assessment comprising:
    one or more audio capture devices configured to capture audio of a speech of a user and convert the audio to audio signals; and
    processing circuitry configured to:
        identify a plurality of conditions, using the audio signals, that result in user hearing difficulty and an indication of the user hearing difficulty wherein the conditions comprise (i) at least one of specific words, phrases, frequencies, or phonemes, and (ii) environmental audio conditions;

generate a hearing profile for the user based on the identified conditions associated with user hearing difficulty, the processing circuitry configured to predict, using the hearing profile, whether a phrase spoken by the individual other than the user will result in the user hearing difficulty for the user given environmental audio conditions; and adjust an operation of an audio output device using the hearing profile and the predicting result to reduce a frequency of user hearing difficulty if the user requires audio enhancement.

2. The audio system of claim 1, wherein the processing circuitry is configured to generate the hearing profile by:
   obtaining a plurality of training data in a controlled environment;
   generating a database using the plurality of training data; and
   using a neural network to generate the hearing profile for the user based on the database;
   wherein the plurality of training data comprises a plurality of the conditions associated with user hearing difficulty.

3. The audio system of claim 1, wherein the processing circuitry is configured to identify the plurality of conditions and generate the hearing profile by:
   converting the audio signals to textual information of spoken words, sentences, or phrases;
   identifying indications of the user hearing difficulty in the textual information, wherein the indications of the user hearing difficulty comprise any of spoken words, sentences, or phrases;
   recording the conditions that are followed by the indications of the user hearing difficulty, and record conditions that are not followed by the indications of the user hearing difficulty; and
   generating the hearing profile based on the recorded conditions that are followed by the indications of the user hearing difficulty and the recorded conditions that are not followed by the indications of the user hearing difficulty.

4. The audio system of claim 3, wherein the processing circuitry is configured to record conditions that are followed by the indications of user hearing difficulty and conditions that are not followed by the indications of user hearing difficulty over a time period for the user.

5. The audio system of claim 1, wherein the processing circuitry is configured to compare the hearing profile for an individual user to a plurality of hearing profiles of other users to determine if the individual user requires audio enhancement.

6. The audio system of claim 1, wherein the hearing profile includes an audiogram.

7. The audio system of claim 1, wherein the processing circuitry is configured to generate a model that predicts user hearing difficulty for the user using the conditions associated with the user hearing difficulty given one or more input conditions.

8. A method for assessing a user's hearing ability and improving audio output of a sound producing device, the method comprising:
   obtaining information of a user's speech using audio signals;
   identifying one or more indications of hearing difficulty using the information;
   generating, by processing circuitry, a customized hearing profile for the user based on the one or more indications of hearing difficulty and a plurality of conditions that contribute to the hearing difficulty, the plurality of conditions that contribute to the hearing difficulty comprising environmental audio conditions and at least one of specific words, phrases, frequencies, or phonemes of speech of an individual other than the user, the processing circuitry configured to use the customized hearing profile to predict whether a phrase spoken by the individual other than the user will result in the hearing difficulty for the user given environmental audio conditions; and
   adjusting audio output of a sound producing device using the customized hearing profile and the predicting result to reduce a frequency of user hearing difficulty events.

9. The method of claim 8, wherein obtaining information of the user's speech comprises receiving audio signals from an audio capture device and converting the audio signals to textual information.

10. The method of claim 8, wherein the one or more indications of hearing difficulty comprise one or more predetermined spoken words, phrases, or sentences that indicate hearing difficulty.

11. The method of claim 8, wherein the customized hearing profile includes an audiogram.

12. The method of claim 8, further comprising using a neural network to train a model to predict hearing difficulty as a function of one or more input conditions.

* * * * *